United States Patent [19]
Clarkson et al.

[11] Patent Number: 5,770,104
[45] Date of Patent: *Jun. 23, 1998

[54] DETERGENT COMPOSITIONS CONTAINING SUBSTANTIALLY PURE EG III CELLULASE

[75] Inventors: Kathleen A. Clarkson, San Francisco; Edward Larenas, San Carlos; Geoffrey L. Weiss, San Francisco, all of Calif.

[73] Assignee: Genencor International, Inc., Rochester, N.Y.

[ * ] Notice: The term of this patent shall not extend beyond the expiration date of Pat. No. 5,290,474.

[21] Appl. No.: 390,767

[22] Filed: Feb. 17, 1995

Related U.S. Application Data

[60] Continuation of Ser. No. 79,546, Jun. 22, 1993, Pat. No. 5,419,778, which is a division of Ser. No. 707,647, May 30, 1991, Pat. No. 5,290,474, which is a continuation-in-part of Ser. No. 668,640, Mar. 13, 1991, abandoned, which is a continuation-in-part of Ser. No. 593,919, Oct. 5, 1990, abandoned.

[51] Int. Cl.$^6$ .................................................. C11D 3/386
[52] U.S. Cl. .......................... 252/174.12; 252/DIG. 12; 8/101; 8/116.1; 435/209; 435/264
[58] Field of Search ................. 252/174.12, DIG. 12; 435/209, 264; 8/101, 116.1

[56] References Cited

U.S. PATENT DOCUMENTS

| | | | |
|---|---|---|---|
| 3,415,804 | 12/1968 | Polson | 260/112 |
| 4,016,039 | 4/1977 | Schriber | 195/66 R |
| 4,144,130 | 3/1979 | Kula et al. | 195/66 R |
| 4,275,163 | 6/1981 | Gallo | 435/209 |
| 4,343,735 | 8/1982 | Menge et al. | 260/112 R |
| 4,385,443 | 5/1983 | Weissman et al. | 435/6 |
| 4,394,443 | 7/1983 | Weissman et al. | 435/6 |
| 4,435,307 | 3/1984 | Barbesgaard et al. | 252/174.12 |
| 4,439,358 | 3/1984 | Coan et al. | 260/112 B |

(List continued on next page.)

FOREIGN PATENT DOCUMENTS

| | | |
|---|---|---|
| 0 120 528 | 10/1984 | European Pat. Off. . |
| 0 137 280 | 4/1985 | European Pat. Off. . |
| 0 173 397 | 3/1986 | European Pat. Off. . |
| 0 220 016 | 4/1987 | European Pat. Off. . |
| 0 244 234 | 11/1987 | European Pat. Off. . |
| 0 271 004 | 6/1988 | European Pat. Off. . |
| 0 538 977 | 3/1992 | European Pat. Off. . |

(List continued on next page.)

OTHER PUBLICATIONS

Aho, "Structural and functional analysis of *Trichoderma reesei* endoglucanase I expressed in yeast *Saccharomyces cerevisiae*" *FEBS Letters* 291:45–49 (1991).

American Type Culture Collection *Catalogue of Filamentous Fungi* p. 412 (1991).

Anderson et al., "α–Amylase production in aqueous two–phase systems with *Bacillus subtilis*" *Enzymes and Microb. Techol.* 7:333–338 (1985).

Ballance et al. "Transformation of *Aspergillus nidulans* by the orotidine–5'–phosphate decarboxylase gene of *Neurospora crassa*" *Biochem. Biophys. Res. Comm.* 112(1):284–289 (1983).

(List continued on next page.)

*Primary Examiner*—Paul Lieberman
*Assistant Examiner*—Kery Fries
*Attorney, Agent, or Firm*—Christopher L. Stone

[57] ABSTRACT

Disclosed are detergent compositions containing a cleaning effective amount of a surfactant or a mixture of surfactants and from about 0.01 to about 5 weight percent of substantially pure EG III cellulase. Preferably, the detergent composition contains no more than about 5 weight percent of CBH I type components based on the total weight of cellulase proteins. When employed in aqueous wash media, the detergent compositions impart color retention/restoration properties as well as improved softening and feel properties to cotton-containing fabrics.

7 Claims, 8 Drawing Sheets

U.S. PATENT DOCUMENTS

| | | | |
|---|---|---|---|
| 4,443,355 | 4/1984 | Murata et al. | 252/174.12 |
| 4,470,969 | 9/1984 | Pancham et al. | 424/101 |
| 4,472,504 | 9/1984 | Gallo | 435/209 |
| 4,479,881 | 10/1984 | Tai | 252/8.8 |
| 4,487,831 | 12/1984 | Day et al. | 435/99 |
| 4,508,825 | 4/1985 | Kim et al. | 435/210 |
| 4,591,563 | 5/1986 | Paul et al. | 435/193 |
| 4,648,979 | 3/1987 | Parslow et al. | 252/8.8 |
| 4,661,289 | 4/1987 | Parslow et al. | 252/547 |
| 4,683,294 | 7/1987 | Van Wijendaele et al. | 530/371 |
| 4,684,723 | 8/1987 | Dove et al. | 530/351 |
| 4,697,003 | 9/1987 | Coan | 530/380 |
| 4,725,544 | 2/1988 | Tan et al. | 435/200 |
| 4,728,613 | 3/1988 | Brewer et al. | 435/222 |
| 4,738,682 | 4/1988 | Boegh et al. | 8/401 |
| 4,762,788 | 8/1988 | Warzywoda et al. | 435/209 |
| 4,797,361 | 1/1989 | Montenecourt | 435/198 |
| 4,822,516 | 4/1989 | Suzuki et al. | 252/174.12 |
| 4,832,864 | 5/1989 | Olson | 252/174.12 |
| 4,885,249 | 12/1989 | Buxton | 435/172.3 |
| 4,894,338 | 1/1990 | Knowles et al. | 435/172.3 |
| 4,912,056 | 3/1990 | Olson | 435/263 |
| 4,945,053 | 7/1990 | Ito et al. | |
| 4,952,505 | 8/1990 | Cho | 435/209 |
| 4,978,470 | 12/1990 | Suzuki et al. | 252/174.12 |
| 5,006,126 | 4/1991 | Olson et al. | 8/401 |
| 5,045,464 | 9/1991 | Ito et al. | 435/209 |
| 5,073,391 | 12/1991 | DeMars et al. | 426/231 |
| 5,120,463 | 6/1992 | Bjork et al. | 252/174.12 |
| 5,122,159 | 6/1992 | Olson et al. | 8/401 |
| 5,124,066 | 6/1992 | Russell | 252/174.12 |
| 5,139,943 | 8/1992 | Heinsohn et al. | 435/226 |
| 5,151,358 | 9/1992 | Heinsohn et al. | 435/226 |
| 5,232,851 | 8/1993 | Cox et al. | 435/263 |
| 5,246,853 | 9/1993 | Clarkson et al. | 435/263 |
| 5,290,474 | 3/1994 | Clarkson et al. | 252/174.12 |
| 5,298,408 | 3/1994 | Nevalainen et al. | 435/209 |
| 5,318,905 | 6/1994 | Saito et al. | 435/209 |
| 5,328,841 | 7/1994 | Loech et al. | 435/209 |
| 5,352,243 | 10/1994 | Ashizawa et al. | 8/401 |
| 5,419,778 | 5/1995 | Clarkson et al. | 8/116.1 |

FOREIGN PATENT DOCUMENTS

| | | |
|---|---|---|
| 2 108 069 | 9/1971 | France . |
| 21 48 278 | 3/1972 | Germany . |
| 58-36217 | 3/1983 | Japan . |
| 58-54082 | 3/1983 | Japan . |
| 62- 062898 | 3/1987 | Japan . |
| 64-40681 | 2/1989 | Japan . |
| 51-15293 | 5/1993 | Japan . |
| 8909259 | 10/1989 | Norway . |
| 1 368 599 | 10/1974 | United Kingdom . |
| 2 094 826 | 9/1982 | United Kingdom . |
| 2 095 275 | 9/1982 | United Kingdom . |
| 85/04672 | 10/1985 | WIPO . |
| 89/09259 | 10/1989 | WIPO . |
| 90/02790 | 3/1990 | WIPO . |
| 90/15866 | 12/1990 | WIPO . |
| 91/05841 | 5/1991 | WIPO . |
| 91/10732 | 7/1991 | WIPO . |
| 91/13136 | 9/1991 | WIPO . |
| 91/17243 | 11/1991 | WIPO . |
| 91/18978 | 12/1991 | WIPO . |
| 92/03541 | 3/1992 | WIPO . |
| 92/06165 | 4/1992 | WIPO . |
| 92/06183 | 4/1992 | WIPO . |
| 92/06184 | 4/1992 | WIPO . |
| 92/06210 | 4/1992 | WIPO . |
| 92/06221 | 4/1992 | WIPO . |
| 92/07134 | 4/1992 | WIPO . |
| 92/17572 | 10/1992 | WIPO . |
| 92/17574 | 10/1992 | WIPO . |
| 93/15186 | 8/1993 | WIPO . |
| 93/20278 | 10/1993 | WIPO . |
| 94/07983 | 4/1994 | WIPO . |
| 94/07998 | 4/1994 | WIPO . |
| 94/23113 | 10/1994 | WIPO . |

OTHER PUBLICATIONS

Bazin, et al., "Cellulasebehandlung von Cellulosewaren mit Hilfe von Enzymen" *Texile Praxis Internation* 47(10) (Oct. 1992).

Beach et al., "High–frequency transformation of the fission yeast *Schizocaccharomyces pombe*" *Nature* 290:140–142 (1981).

Bealin–Kelly et al, "Studies on the thermostability of the alpha–amylase of bacillus–caldovelox" *Appl. Microbiol. and Biotech* 36(3):332–336 (Dec. 1991).

Beggs, J.D. "Transformation of Yeast by Replicating Hydrid Plasmid" *Nature* 275:104–109 (1978).

Berg et al., "Enzyme–Gold Affinity Labelling of Cellulose" *Journal of Electron Microsc. Tech.* 8(4):371–379 (Apr 1988) Abstract.

Berges and Barreau "Isolation of uridine auxotrophs from *Trichoderma reesei* and efficient transformation with the cloned ura3 and ura5 genes" *Current Genetics* 19:359–365 (1991).

Bhat et al., "The Endo–(1–4)–β–D–Glucanase System of *Penicillium pinophilum* Cellulase: Isolation, Purification, and Characterization of Five Major Endoglucanase Components" *Carbohydrate Research* 190:279–297 (1989).

Bhikhabhai et al., "The cellulotyic enzymes of *trichoderma reesei* as a system of homologous proteins" *FEBS Letters* 169(2):301–309 (Feb. 1984).

Brown and Gritzali, "Microbial Enzymes and Lignocellulose Utilization" *Genetic Control of Environmental Pollutants,* Omenn Editor, Plenum Publisher, pp. 239–265 (1984).

Brosnan, et al., "Investigation of the mechanism of irreversible thermoinactivation of bacillus–stearothermophilus alpha–amylase" *Eur. J. of Biochem.* 203(1–2)225–231 (Jan 1992).

Boucher, et al., "Complete nucleotide sequence of the xylanase gene from the yeast *Cryptococcus albidus*" *Nucleic Acid Research* 16(20):9874 (1988).

Buschle–Diller, et al., "Enzymatic Hudrolysis of Cotton, Linen, Ramie, and Viscose Rayon Fabrics" *Textile Research Journal* "64(5):270–279 (May 1994).

Cannon, P.F., "International Commission on the Taxonomy of Fungi (ICTF): name changes in fungi of microbiological, industrial and medical importance", *Microbiological Sciences* 3:285–287 (1986).

Carter et al., "Chromosomal and genetic analysis of the electrophoretic karyotype of *Trichderma reesei*:mapping of the cellulase and xylanase genes" *Molec. Microb.* 6(15):2167–2174 (1992).

Case et al., "Efficient transformation of *Neurospora crassa* by utilizing hybrid plasmid DNA" *Proc. Natl. Acad. Sci. USA* 76(10):5259–5263 (1979).

Case, "Genetical and Molecular Analyses of QA–2 Transformants in *Neurospora crassa*" *Genetics* 113:569–587 (1986).

Chauthaiwale, et al., Molecular cloning of xylanase genes from Chainia in *E. coli* gene cloning; plasmid pUC8, plasmid pTZ18R–based vector constuction and expression in *E. coli Abstr. Gen. Meet. Am. Soc. Microbiol.* 91 Meet. 189 (1991) [Abstract].

Chen at al., "Nucleotide Sequence and Deduced Primary Structure of Cellobiohydrolase II from *Trichoderma reesei*" *Biotechnology* 5:274–278 (1987).

Clarke, D., "Enzyme treatment for removing pills from garment dyed goods" *International Dyer* 178(7):20–21 (1993).

Corrick et al., "The Nucleotide Sequence of the amdS Gene of *Aspergillus nidulans* and the Molecular Characterization of 5' Mutations" *Gene* 53:63–71 (1987).

Coughlan et al., "Comparative Biochemistry of Fungal and Bacterial Cellulolytic Enzyme Systems" *Biochemistry and Genetics of Cellulose Degradation* Aubert et al Eds., pp. 11–30 (1988).

Dhawale et al., "Transformation of *Neurospora crassa* with circular and linear DNA and analysis of the fate of the transforming DNA" *Current Genetics* 10:205–212 (1985).

Ellouz et al., "Analytical separation of Trichoderma reesei cellulases by ion–exchange fast proetein liquid chromatography" *J. of Chromatography* 396:307–317 (1987) [Abstract].

Fincham, "Transformation in Fungi" *Microbiol. Rev.* 53:148–170 (1989).

Fukusaki, et al., The complete nuclotide sequence of the xylanase gene (xynA) of *Bacillus pumilus FEBS 1512* 171(2):197–201 (Jul 1984).

Gilkes et al., "Domains in Microbial β–1,4–Glycanases:Sequence Conservation, Function and Enzyme Families" *Microbiological Reviews* 55:303–315 (1991).

Gong, et al., "Biosynthesis, Pruification, and Mode of Action of Cellulases of *Trichoderma reesei*" *Hydrolysis of Cellulose* pp. 261–287 (1979).

Gruber et al., "Cloning of the *Trichoderma reesei* pyrG gene and its use as a homologous marker for a high–frequency transformation system" *Current Genetics* 18:447–451 (1990).

Gruber et al., "The development of a heterologous transformation system for the cellulolytic fungus *Trichoderma reesei* based on pyrG–negative mutant strain" *Current Genetics* 18:71–76 (1990).

Hakansson et al., "Purification and characterization of a Low Molecular Weight 1,4–β–Glucan Glucanohydrolase from the Cellulolytic Fungus *Trichoderma Viride* OM 9414" *Biochimica et Biophysica Acta* 524:385–392 (1978).

Hakansson, Dissertation, Faculty of Science, Uppsal University, pp. 6–23 (1981).

Harkki et al., "Genetic engineering of Trichoderma to produce strains with novel cellulase profiles" *Enzyme Microb. Technol.* 13:227–233 (1991).

Hayashida et al., "Production and Purification of Thermostable Cellulases from *Humicola insolens*" *Agric. Biol. Chem.* 44(8):1721–1728 (1980).

Hayashida et al., "The Role of Carbohydrate Moiety on Thermostability of Cellulases from *Humicola insolens* YG–8" *Agri. Biol. Chem.* 44(3):481–487 (1980).

Hayashida, et al., "Cellulases of *Humicola insolens* and *Humicola grisea*" Methods in Enzymology 160:323–332 (1988).

Hinnen, A. et al., "Transformation of yeast" *Proc. Natl. Acad. Sci. USA* 75(4):1929–1933 (1978).

Innovations, "Back Staining. A Problem? Not Anymore!" 2 pages (1991).

*International Textile Bulletin, Dyeing/Printing/Finishing,* "Softening and Polishing of Cotton Fabrics by Cellulase Treatment" (2nd Quarter, 1990) pp. 5–8 (1990).

Irie et al., *Hakkikogaku Kaishi* 86(6):457–464 (1990) [Abstract].

JTN "Weight Loss Treatment to Soften the Touch of Cotton Fabric" p. 64 (Dec. 1988).

Kenkyushitsu et al., "The Improvement of Cellulose Fibers by Means of Cellulase" pp. 54–61.

Kim et al., Transformation of *Neurospora crassa* with trp–1 gene and the effect of host strain upon the fate of the transforming DNA *Current Genetics* 13:65–70 (1988).

Kimmel, A., Selection of Clones from Libraries:Overview *Methods in Enzymology* 152:393–399 (1987).

Knowles et al., "The use of gene technology to investigate fungal cellulolytic enzymes *Trichoderma reesei* cellulase complex gene cloning and expression in *Saccharomyces cerevisiae*" *FEMS Symp.* 43:153–169 (1988). [Abstract].

Knowles et al., "The use of gene technology in the development of novel cellulolytic organisms–*Trichoderma reesei* cellulase and celluloiohydrolase gene cloning and expression; a review" *Recent Adv. Biotechnol. Appl. Biol.* pp. 139–142 (1988) [Abstract].

Kochavi et al., "Optimizing Processing conditions in Enzymatic Stonewashing" *Amer. Dystruff Reporter,* pp. 24, 26 and 28 (Sep. 1990).

Kubicek–Pranz et al., "Characterization of Commercial *Trichoderma–reesei* Cellulase Preparations by Denaturing Electrophoresis SDS–PAGE and Immunostaining Using Monoclonal Antibodies" *Biotechnol. Appl. Biochem.* 14(3):317–323 (1991) [Abstract].

Kubicek–Pranz et al., "Transformation of *Trichoderma reesei* with cellobiohydrolase II gene as a means for obtaining strains with increased cellulase production and specific activity" *Journal of Biotechnology* 20:83–94 (1991).

Kula et al., "Purification of Enzymes by Liquid–Liquid Extraction" pp. 73–118.

Kyviacou et al., *Enzyme Microb. Technology* 9(1):25–32 (1987).

Lappalainen et al., *Biotechnol. Appl. Biochem* 8(5):437–45 [abstract].

Lopes et al., "High–copy–number integration into the ribosomal DNA of Saccaromyces cerevisiae: a new vector for high–level expression–plasmid pMIRY2 construction with ribosome DNA; phosphoglycerate–kinase, superoxide–dismutase and thaumatin gene cloning" *Gene* 79(2):199–206 (1989) [Abstract].

Luderer et al., "A Re–appraisal of Multiplicity of Endoglucanase I from *Trichoderma reesei* Using Monoclonal Antibodies and Plasma Desorption Mass Spectrometry" *Biochim. Biophys. Acta* 1076:427–434 (1991) [Abstract].

Messner et al., "Cellobiohydrolase II is the main conidial–bound cellulase in *Trichoderma reesei* and other Trichoderma strains" *Archives of Microbiology* 155(6):601–606 (1991).

Miller et al., "Direct and Indirect Gene Replacements in *Aspergillus nidulans*" *Mol. and Cell. Biol.* 5(7):1714–1721 (1985).

Murphy–Holland et al., "Secretion activity and stability of deglycosulated cellulase of *Trichoderma reesei* gene cloning" *Abstr. Annu. Meet. Am. Soc. Microbiol.* 85th Meeting, vol. 193 (1985) [Abstract].

Nevalainen, H., "Genetic improvement of enzyme production in industrially important fungal strains" *Technical Research Center of Finland, Publications* 26:39–41 (1985).

Novo Enzymes, Celluclast, 4 pages.

Ohishi et al., "Reformation of Cotton Fabric by Cellulase" pp. 1–12.

Paietta, J.V. et al., "Gene disruption by transformation in *Neurospora crass*" *Mol. Cell. Biol.* 5(7):1554–1559 (1985).

Pentilla et al., "Construction of brewer's yeast secreting fungal endo–beta glucanase–recombinant cellulase preparation by protein secretion by Saccharomyces cerevisiae transformation" *Current Genetics* 12(6):413–420 (1987) [Abstract].

Penttila et al., "Homology between cellulase genes of *Trichoderma reesei*:complete nucleotide sequence of the endoglucanase I gene" *Gene* 45:253–263 (1986).

Penttila et al., "Expression of Two *Trichoderma reesei* Endoglucanases the Yeast *Saccharomyces cerevisiae*" *Yeast* 3:175–185 (1987).

Reinikainen et al., "How do *Trichoderma reesei* cellobiohydrolase bind to and degrad cellulose?—cellobiohydrolase and cellulase characterization", *Abstr. Pap. Am. Chem. Soc.* 202 Meet. Pt. 1, (1991) [Abstract].

Royer et al., "Xylanase of Trichoderma longibrachiatum production and characterization" *Abstr. Annul. Meet. Am. Soc. Microlbiol.*, 85th Meet. 236 (1985) [abstract].

Saddler et al., Purification and application of hemicellulose modifying enzymes—*Trichoderma reesei* large–scale endo–1,4–beta–D–xylanase production; xylan degradation *Am. Chem. Soc.* 195 Meeting, Cell 198 (1988) [abstract].

Saloheimo et al., "EGIII a new endoglucanase from *Trichoderma reesei;* the characterization of both gene and enzyme" *Gene* 63:11–21 (1988).

Sambrook et al., *Molecular Cloning A Laboratory Manual* 2nd Ed. Cold Spring Harbor Laboratory Press, pp. 1.53–1.73 (1989).

Schülein, "Cellulases of *Trichoderma reesei*" *Methods in Enzymology* 160:234–242 (1988).

Seiboth et al., "Disruption of the *Trichoderma reesei* cbh2 gene coding for cellobiohydrolase II leads to a delay in the triggering of cellulase formation by cellulose" *J. Gen. Microb.* 138:1259–1264 (1992).

Sheir–Neiss et al., "Characterization of the Secreted Celluloses of *Trichoderma reesei* Wild Type and Mutants During Controlled Fermentations" *Appl. Microbiol. Biotechnol.* 20:46–53 (1984).

Shoemaker et al., "Characterization and Properties of Cellulases Purified from *T. reesei* strain L27" *Bio/Technology* 687–690 (1983).

Shoemaker et al., "Molecular Cloning of Exo–cellobiohydrolase I Derived from *Trichoderma reesei* Strain L27" *Biotechnology* pp. 691–695 (1983).

Smith et al., "Sequence of the Cloned pyr4 Gene of *Trichoderma reesei* and its use as a Homologous Selectable Marker for Transformation" *Current Genetics* 19:27–33 (1991).

Stahl, U. et al., "Replication and expression of a bacterial–mitochondrial hybrid plasmid in the fungus *Podospora anserina*" *Proc. Natl. Acad. Sci. USA* 79:3641–3645 (1982).

Teeri et al., "Engineering Trichoderma and its cellulases *Trichoderma reesei* cellulase and cellobiohydrolase gene cloning and expression: potential strain improvement and enzyme engineering" *Trichoderma reesei Cellulases* pp. 156–167 (1990) [abstract].

Teeri et al., "Homologous domainsn in *Trichoderma reesei* cellulolytic enzymes: gene sequence and expression of cellobiohydrolase II" *Gene* 51:43–52 (1987).

Teeri, "The Cellulolytic Enzyme System of *Trichoderma reesei*" *VTT Publications* 38, pp. 1–52 + Appendices 41 pps. (1987).

Tenkanen et al., "Two major xylanases of *Trichoderma–reesei*" *Enzyme Microb Technol.* 14(7):566–574 (1992).

Thomas, K., "Site–Directed Mutagenesis by Gene Targeting in Mouse Embryo–Derived Stem Cells" *Cell* 51:503–512 (Nov. 1987).

Toronnen et al., "The major xylanases of *Trichoderma reesei:* purification, and production of monoclonal antibodies" *Progress in Biotechnology* 7:501–504 (1992).

Toronnen et al., "The Two Major Xylanases from *Trichoderma reesei:* Characterization of Both Enzymes and Genes" *Bio/Technology* 10(11):1461–1465 (1992).

Tudzynski, P. et al., Transformation to senescence with plasmid–like DNA in the Ascomycete *Podospora anserina Current Genetics* 2:181–184 (1980).

Tyndall, R., "Improving the Softness and Surface Appearance of Cotton Fabrics and Garments by Treatment with Cellulase Enzymes" *Textile Chemist and Colorist* 24(6):23–26 (Jun. 1992).

U.S. Department of Health, Education and Welfare, Public Health Service, National Institutes of Health, "Modification of certified host–vector systems" *Recombinant DNA Technical Bulletin,* 2:132–134 (1979).

Ujiie et al., "Low molecular weight xylanase from *Trichoderma viride*" endo–1,4–beta–D–xylanases purification and characterization *Appl. Env. Microb.* 57(6):1860–62 (1991) [Abstract].

Ulker et al., "Characterization of an Unglycosylated Low Molecular Weight 1,4–β–glucan–glucanohydrolase of *Trichoderma reesei*" *FEMS Microbiology Letters* 69:215–219 (1990).

Ulrich, R.C. et al., "Transforming Basidiomycetes" *Molecular Genetics of Filamentous Fungi;* Alan R. Liss, Inc., pp. 39–57 (1985).

Uusitalo et al., "Enzyme Production by recombinant *Trichoderma reesei* strains" *Journal of Biotechnology* 17:35–50 (1991).

Van Arsdell et al., "Cloning, Characterization and Expression in *Saccharomyces Cervisiae* of Endoglucananse I from *Trichoderma reesei*" *Bio/Technology* 5:60–64 (1987).

Voragen et al., "Cellulases of a Mutant Strain of *Trichoderma Viride* QM 9414", *Methods in Enzymology* 160:243–251 (1988).

Wilson et al., "Sequence of the *Aspergillus niger* pyrG Gene" *Nucl. Acids Res.* 16:2339 (1988).

Wilson et al., "Expression Vector pT7:TKII for the Synthesis of Authentic Biologically Active RNA Encoding Vaccinia Virus Thymidine Kinase" *Gene* 77:69–78 (1984).

Winnacker *From Genes to Clones Introduction to Gene Technology,* ed. Michael Weller, New York, New York 1987.

Wood, "Properties of Cellulolytic Enzyme Systems" *Biochem. Soc. Trans.* 13(2):407–410 (1985).

Wood et al., "The Mechanism of Fungal Cellulose Action" *Biochem J.* 260:37–43 (1989).

Wood et al., "Methods for Measuring Cellulase Activities" *Methods in Enzymology* 160:87–112 (1988).

Wood et al., "Aerobic and Anaerobic Fungal Cellulases, With Special Reference to Their Mode of Attack on Crystalline Cellulose" *Biochemistry and Genetics of Cellulose Degradation* pp. 31–52 (1988).

Wozney, "Using Purified Protein to Clone Its Gene" *Methods in Enzymology* 182:738–751 (1990).

Yamada et al., "Synthesis and Reaction of New Type I–N Ylide, N–tosyliminoiodinane" *Chem Letters* pp. 361–262 (1975).

Yamagishi, "Reforming of Cellulosic Fiber With Cellulose" *The Shizuoka Prefectural Hamamatsu Textile Industrial Research Institute Report* 24:54–61 (1986).

Yang, et al., "Nucelotide sequence of a *Bacillus circulans* xylanase gene" *Nucleic Acids Res.* 16(14):7187.

Yanish–Perron et al., "Improved M13 phage cloning vectors and host strains:nucleotide sequences of the M13mp18 and pUC19 cecotrs" *Gene* 33:103–119 (1985).

Young, et al., "Efficient isolation of genes by using antibody probes" *Proc. Natl. Acad. Sci.* 80:1194–1198 (Mar. 1983).

Zappe, et al., Nucleotide sequence of a *Clostridium acetobutylicum* P262 xylanase gene (xynB).

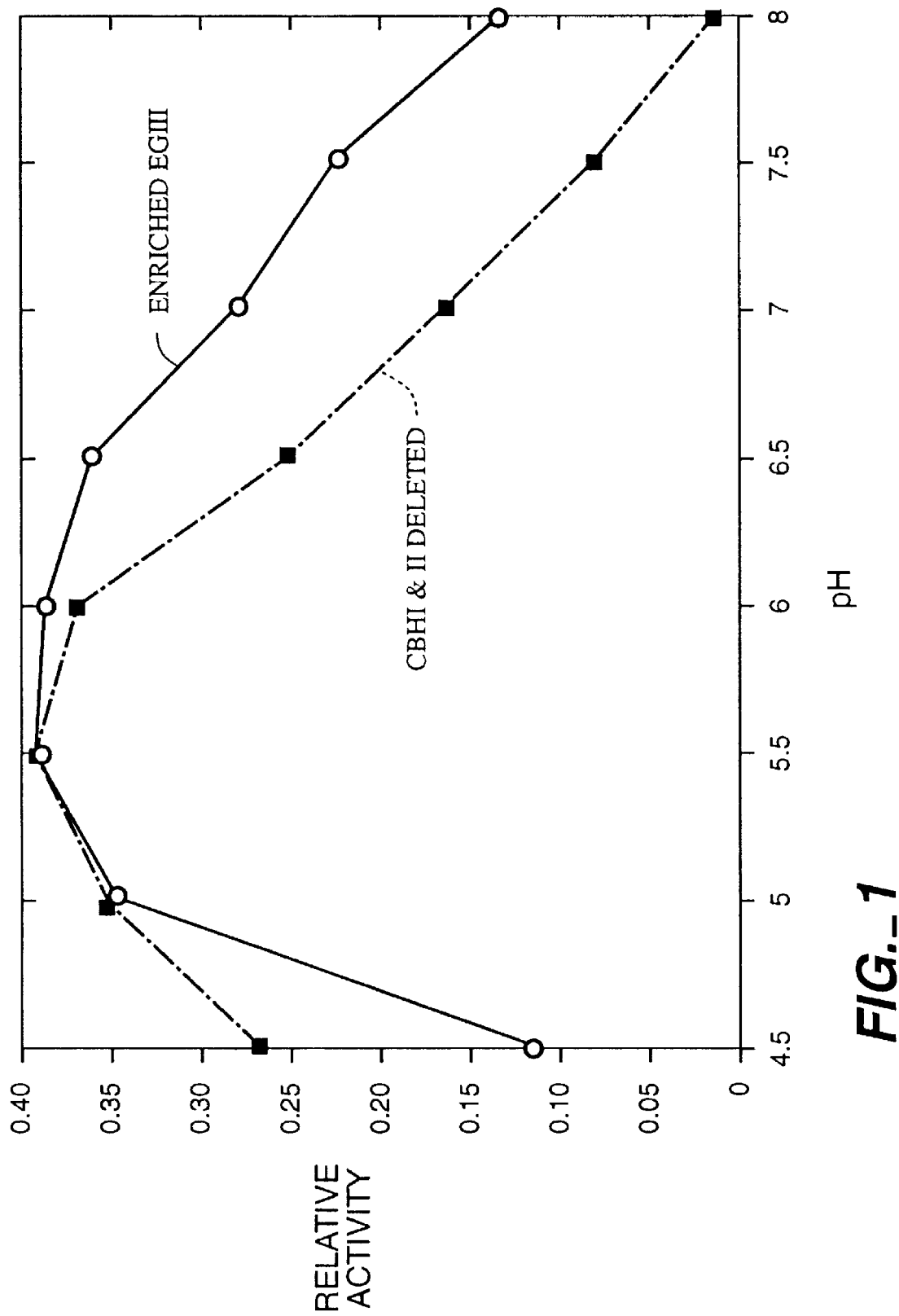
FIG._1

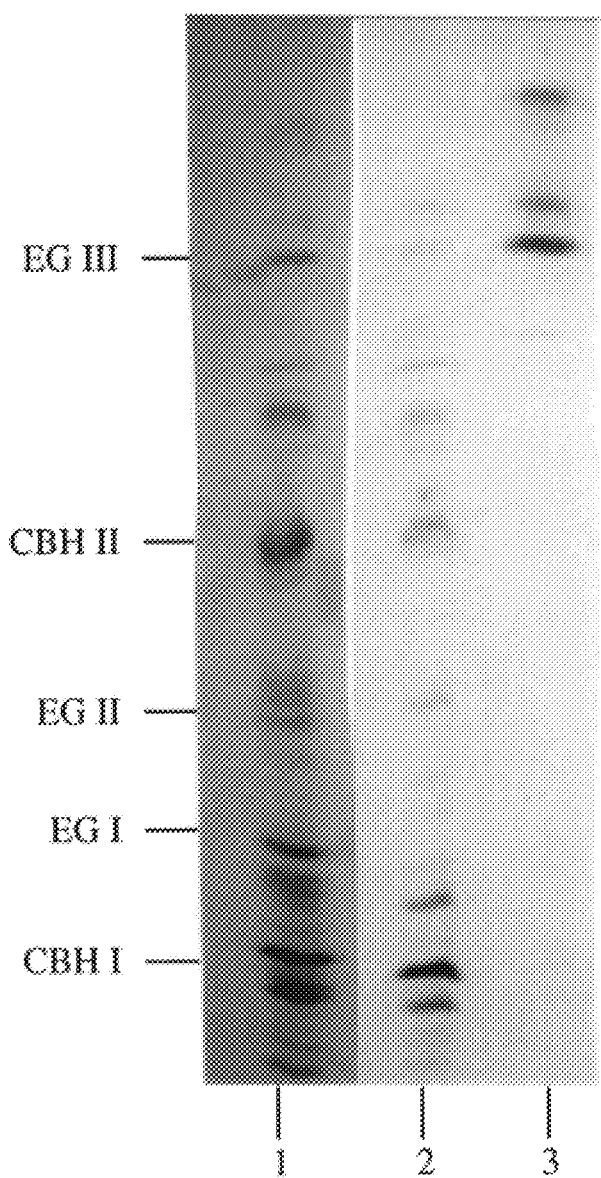
FIG._2

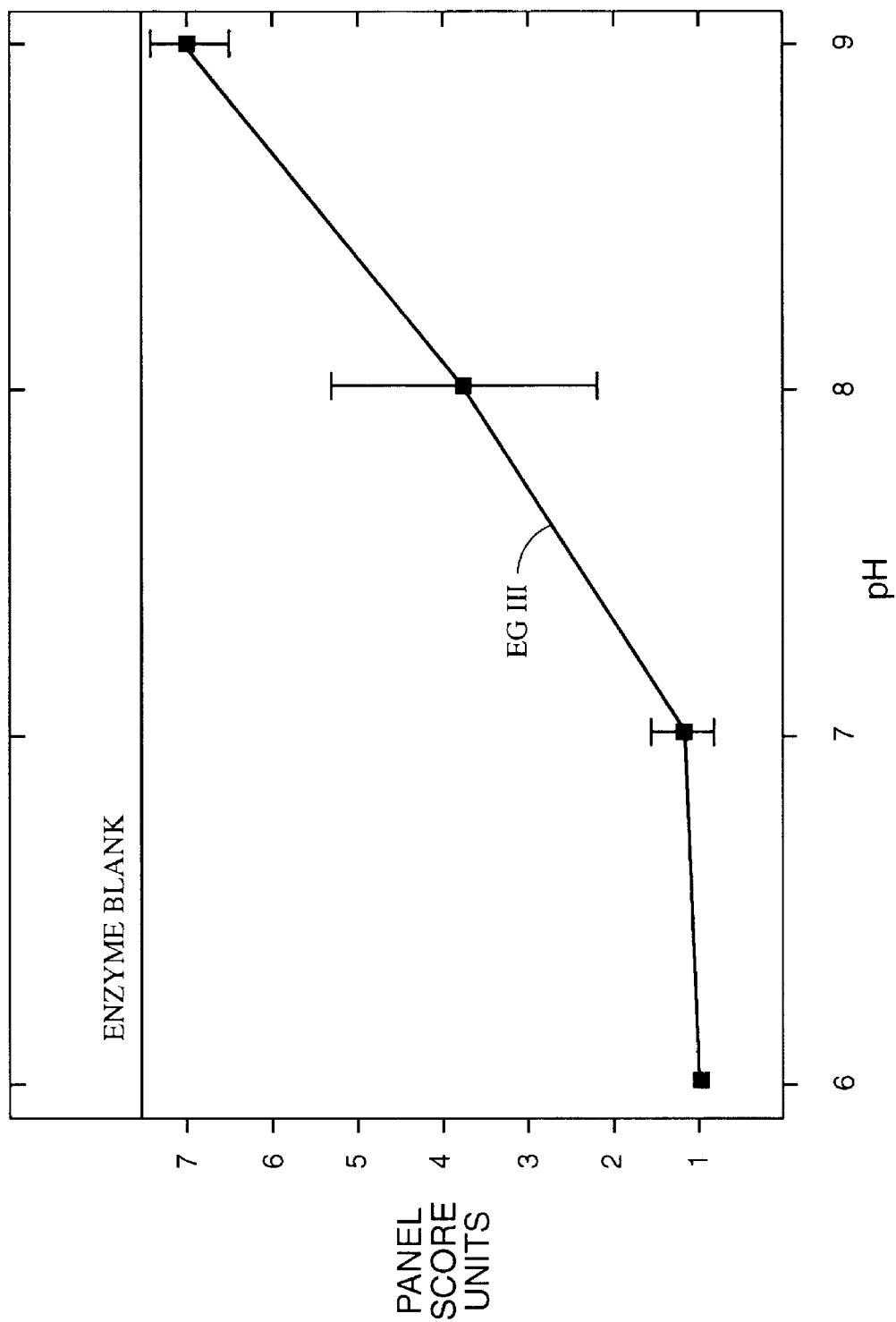
FIG._3

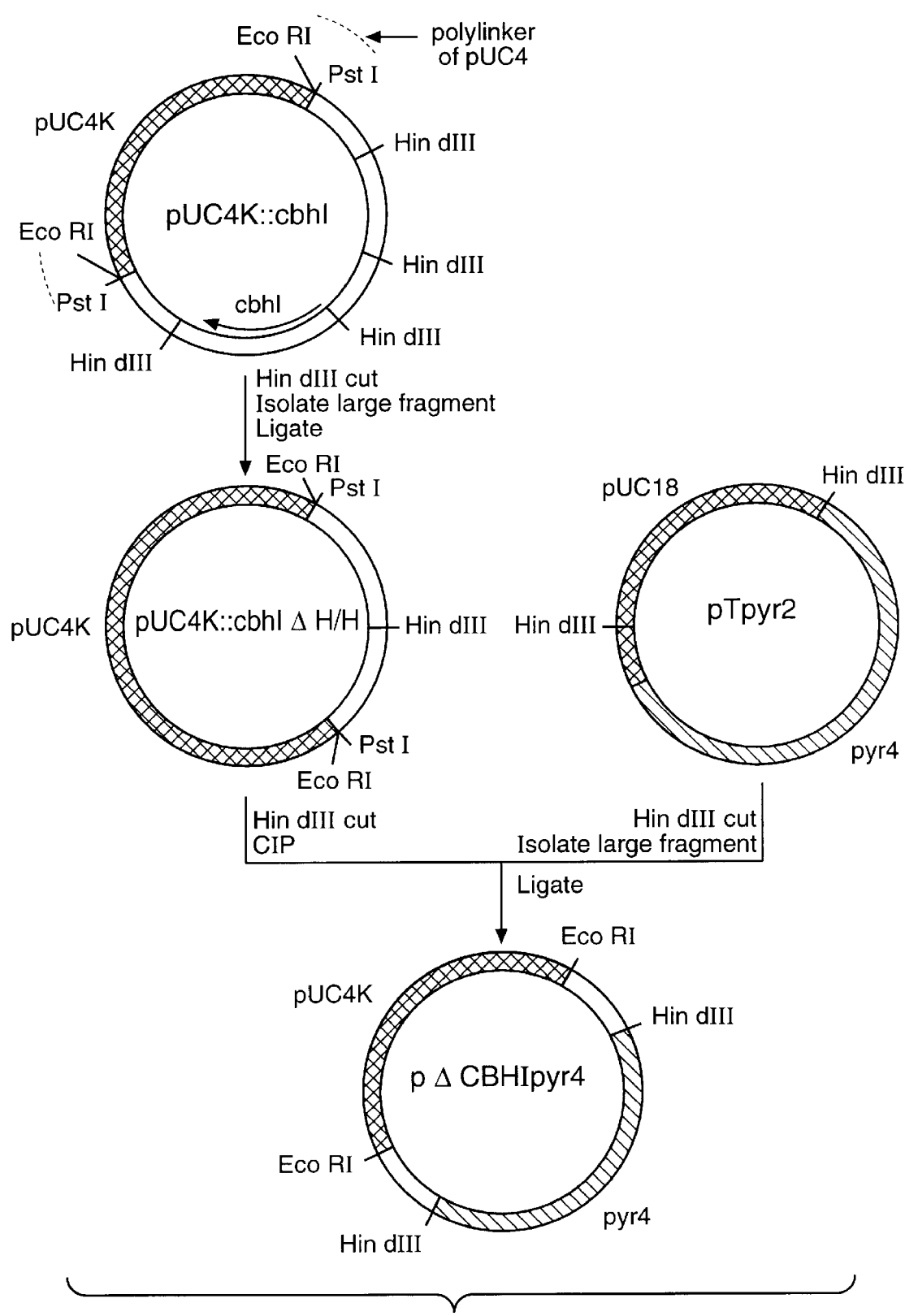
FIG._4

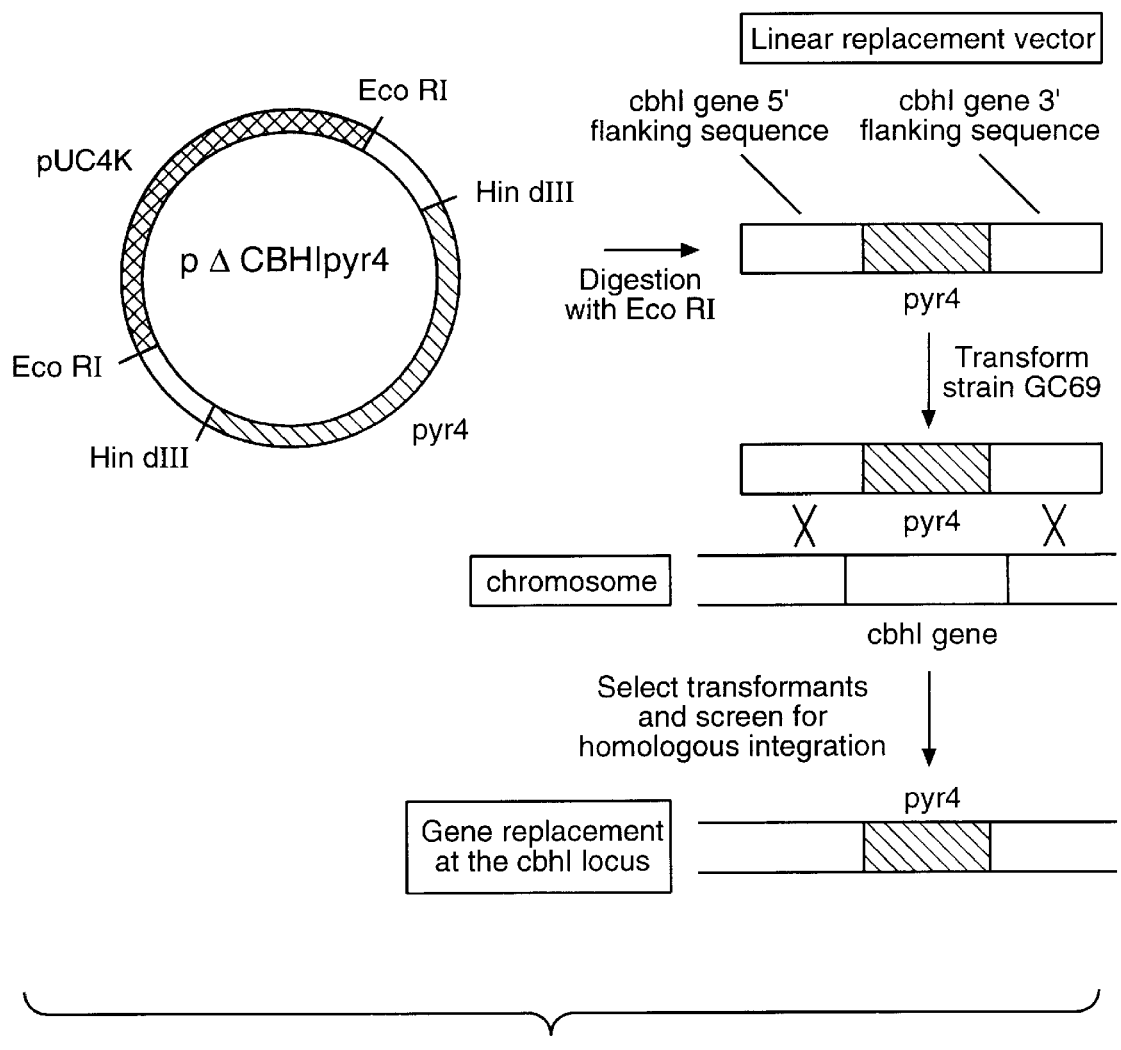
FIG._5

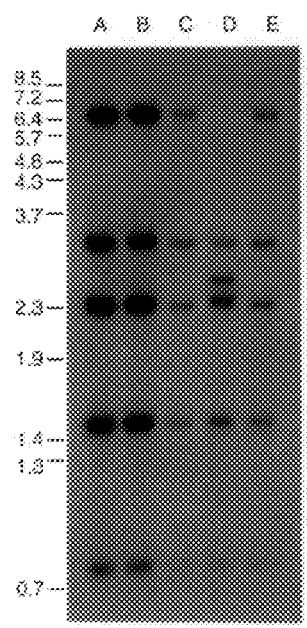
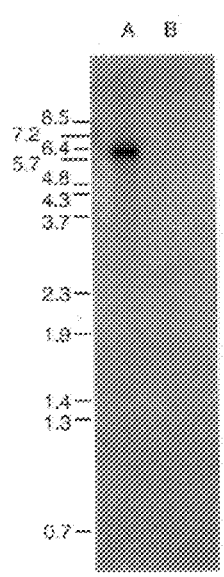
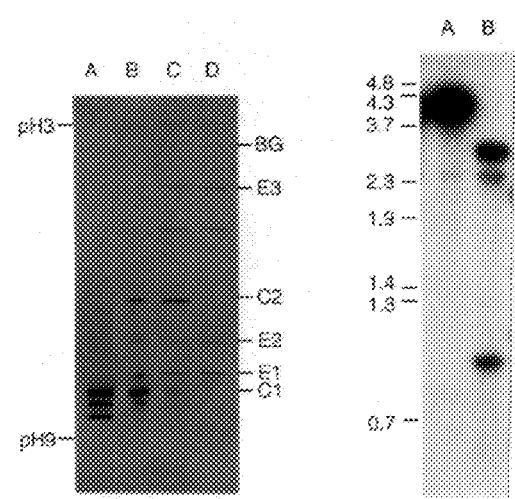
FIG._6  FIG._7  FIG._8  FIG._10

FIG._9A
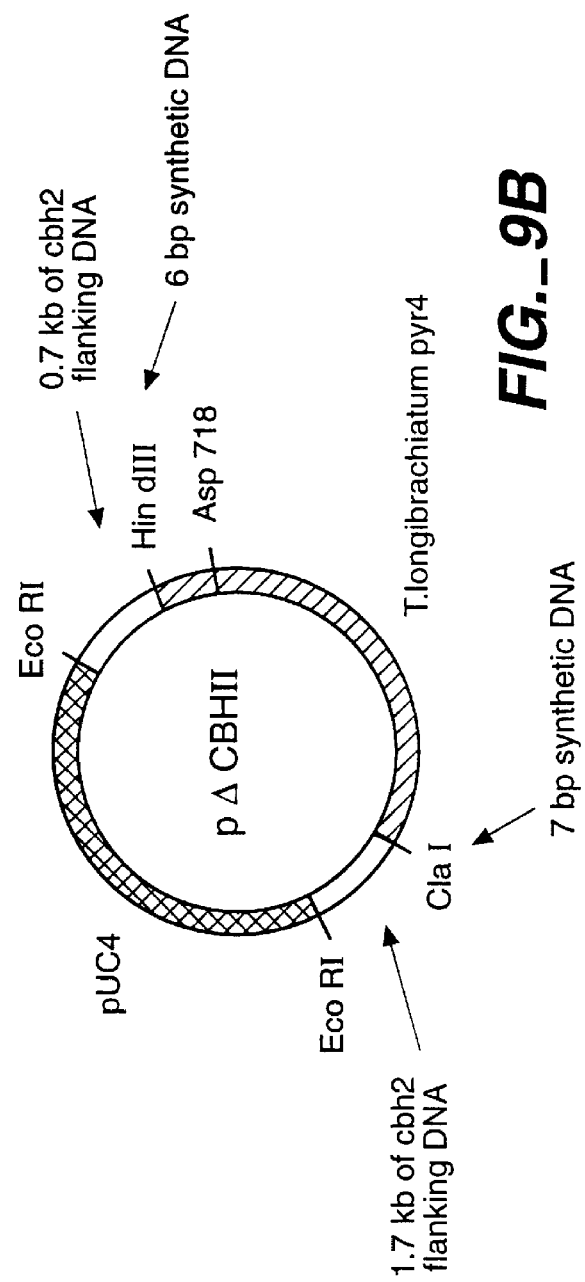
FIG._9B

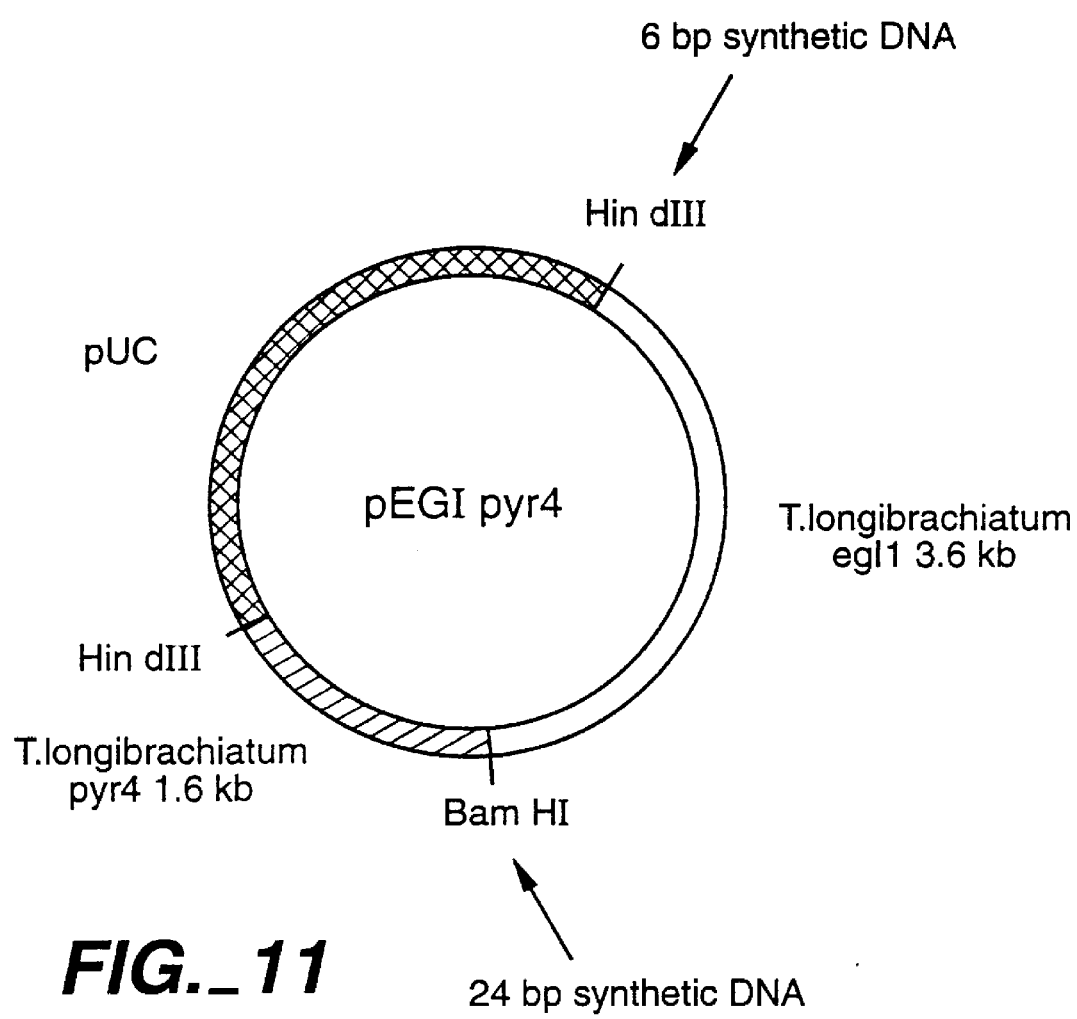
FIG._11

DETERGENT COMPOSITIONS CONTAINING SUBSTANTIALLY PURE EG III CELLULASE

CROSS-REFERENCE TO RELATED APPLICATIONS

This application is a continuation of U.S. patent application Ser. No. 08/079,546, filed Jun. 22, 1993, now U.S. Pat. No. 5,419,778, which is a divisional of U.S. patent application Ser. No. 07/707,647 filed on May 30, 1991, now U.S. Pat. No. 5,290,474, which is a continuation-in-part of U.S. patent application Ser. No. 07/688,640 filed Mar. 13, 1991, now abandoned, which is a continuation-in-part of U.S. patent application Ser. No. 07/593,919, filed Oct. 5, 1990, now abandoned, the disclosure of these latter two applications are incorporated herein in their entirety by reference.

BACKGROUND OF THE INVENTION

1. Field of the Invention

The present invention is directed to detergent compositions containing substantially pure EG III cellulose from Trichoderma spp. as well as to methods for employing such compositions. In particular, the detergent compositions of the present invention comprise a cleaning effective amount of one or more surfactants and substantially pure EG III cellulase.

2. State of the Art

Cellulases are known in the art as enzymes that hydrolyze cellulose (β-1,4-glucan linkages) thereby resulting in the formation of glucose, cellobiose, cellooligosaccharides, and the like. While cellulases are produced (expressed) in fungi, bacteria and the like, cellulase produced by certain fungi and, in particular by the fungal class Trichoderma Sp. (especially *Trichoderma longibrachiatum*), have been given the most attention because a complete cellulase system capable of degrading crystalline forms of cellulose is readily produced in large quantities via fermentation procedures.

In regard to the above, Schulein., "Methods in Enzymology", 160, 25, pages 234 et seq. (1988), disclose that complete fungal cellulase systems comprise several different enzyme classifications including those identified as exo-cellobiohydrolases (EC 3.2.1.91) ("CBH"), endoglucanases (EC 3.2.1.4) ("EG"), and β-glucosidases (EC 3.2.1.21) ("BG"). The fungal cellulose classifications of CBH, EG and BG can be further expanded to include multiple components within each classification. For example, multiple CBHs and EGS have been isolated from a variety of fungal sources.

The complete cellulase system comprising CBH, EG and BG components is required to efficiently convert crystalline cellulose to glucose. Isolated components are far less effective, if at all, in hydrolyzing crystalline cellulose. Moreover, a synergistic relationship is observed between the cellulase components particularly if they are of different classification.

On the other hand, cellulases and components thereof, used either singularly or in combination, are also known in the art to be useful in detergent compositions. For example, endoglucanase components of fungal cellulases have been used for the purposes of enhancing the cleaning ability of detergent compositions, for use as a softening agent, and for use in improving the feel of cotton fabrics, and the like. However, there is a problem with using the EG I and EG II components derived from Trichoderma spp. and especially *Trichoderma longibrachiatum* in detergent compositions. Specifically, such components have their maximal activity at acidic pHs whereas most laundry detergent compositions are formulated for use at neutral or alkaline (pH>7 to about 10) conditions. Whiles it is disclosed in U.S. Ser. No. 07/668,640 that the use of one or more acidic endoglucanase components of *Trichoderma longibrachiatum* in detergent compositions will provide improvements in softening, color retention/restoration and feel to cotton-containing fabrics even when treated under alkaline conditions, the present invention is directed to the discovery that the EG III component of Trichoderma spp. provides for superior and unexpected advantages in detergent compositions as compared to the EG I and EG II components of *Trichoderma longibrachiatum*.

Specifically, this component has been found to possess significant enzymatic activity under alkaline conditions.

SUMMARY OF THE INVENTION

The present invention is directed to the use of substantially pure EG III cellulase in detergent compositions to attain improvements in softening, color retention/restoration and feel. Specifically, because of the surprisingly enhanced activity of EG III cellulose under alkaline conditions, detergent compositions containing substantially pure EG III cellulase are particularly suited for use in laundry conditions where a neutral or alkaline detergent wash medium is employed.

Accordingly, in one of its composition aspects, the present invention is directed to a detergent composition comprising a cleaning effective amount of a surfactant or a mixture of surfactants and from about 0.01 to about 5 weight percent, and preferably from about 0.05 to about 2 weight percent, of a substantially pure EG III cellulase.

In one of its method aspects, the present invention is directed to a method for enhancing the softness of a cotton-containing fabric which method comprises washing the fabric in a wash medium derived from a detergent composition comprising a cleaning effective amount of a surfactant or a mixture of surfactants and from about 0.01 to about 5, and preferably from about 0.05 to about 2, weight percent of substantially pure EG III cellulase.

In another of its method aspects, the present invention is directed to a method for retaining/restoring the color of a cotton-containing fabric which method comprises washing the fabric one or more times in a wash medium derived from a detergent composition comprising a cleaning effective amount of a surfactant or a mixture of surfactants and from about 0.01 to about 5, and preferably from about 0.05 to about 2, weight percent of substantially pure EG III cellulase.

BRIEF DESCRIPTION OF THE DRAWINGS

FIG. 1 illustrates the RBB-CMC activity profile over a pH range at 40° C. for an EG enriched fungal cellulase composition derived from a strain of *Trichoderma longibrachiatum* transformed so as to be incapable of expressing CBH I and CBH II; as well as the activity profile of an enriched EG III cellulase composition derived from *Trichoderma longibrachiatum* over a pH range at 40° C.

FIG. 2 is an isoelectric focusing gel which, in Lane 1, displays the proteins expressed by a wild type *Trichoderma longibrachiatum*; in Lane 2 displays the proteins expressed by a strain of *Trichoderma longibrachiatum* transformed so as to be incapable of expressing EG I and EG II components; and in Lane 3 displays the proteins found in substantially pure EG III cellulase. The left hand margin of this figure is marked so as to identify the bands attributable to CBH I, CBH II, EG I, EG II and EG III.

FIG. 3 illustrates the fiber removal properties and hence the color restoration properties of EG III at various pH's.

FIG. 4 is an outline of the construction of pΔCBHIpyr4.

FIG. 5 illustrates deletion of the *Trichoderma longibrachiatum* cbh1 gene by integration of the larger EcoRI fragment from pΔCBHIpyr4 at the cbh1 locus on one of the *Trichoderma longibrachiatum* chromosomes.

FIG. 6 is an autoradiograph of DNA from a *Trichoderma longibrachiatum* strain GC69 transformed with EcoRI digested pΔCBHIpyr4 after Southern blot analysis using a $^{32}$P labelled pΔCBHIpyr4 as the probe.

FIG. 7 is an autoradiograph of DNA from a *Trichoderma longibrachiatum* strain GC69 transformed with EcoRI digested pΔCBHIpyr4 after Southern blot analysis using a $^{32}$P labelled pIntCBHI as the probe.

FIG. 8 is an isoelectric focusing gel displaying the proteins secreted by the wild type and by transformed strains of *Trichoderma longibrachiatum*. Specifically, in FIG. 8, Lane A of the isoelectric focusing gel employs partially purified CBH I from *Trichoderma longibrachiatum*; Lane B employs protein from a wild type *Trichoderma longibrachiatum*; Lane C employs protein from a *Trichoderma longibrachiatum* strain with the cbh1 gene deleted; and Lane D employs protein from a *Trichoderma longibrachiatum* strain with the cbh1 and cbh2 genes deleted.

In FIG. 8, the right hand side of the figure is marked to indicate the location of the single proteins found in one or more of the secreted proteins. Specifically, BG refers to β-glucosidase; E1 refers to endoglucanase I; E2 refers to endoglucanase II; E3 refers to endoglucanase III; C1 refers to exo-cellobiohydrolase I; and C2 refers to exo-cellobiohydrolase II.

FIG. 9A is a representation of the *Trichoderma longibrachiatum* cbh2 locus cloned as a 4.1 kB EcoRI fragment of genomic DNA and FIG. 9B is a representation of the cbh2 gene deletion vector, pPΔCBHII.

FIG. 10 is an autoradiograph of DNA from a *Trichoderma longibrachiatum* strain P37PΔCBHI transformed with EcoRI digested pPΔCBHII after Southern blot analysis using a $^{32}$P labelled pPΔCBHII as the probe.

FIG. 11 is a diagram of the plasmid pEGI pyr4.

DETAILED DESCRIPTION OF THE INVENTION

As noted above, the present invention generally relates to detergent compositions containing substantially pure EG III cellulose as well as for methods employing such detergent compositions. When used in aqueous wash media at alkaline pH's, such compositions are particularly effective in imparting improvements in softening, color retention/restoration, and feel to the treated cotton-containing fabric.

However, prior to discussing this invention in detail, the following terms will first be defined.

The term "EG III cellulase" refers to the endoglucanase component derived from Trichoderma spp. characterized by a pH optimum of about 5.5 to 6.0, an isoelectric point (pI) of from about 7.2 to 8.0, and a molecular weight of about 23 to 28 Kdaltons. Preferably, EG III cellulase is derived from either *Trichoderma longibrachiatum* or from *Trichoderma viride*. EG III cellulase derived from *Trichoderma longibrachiatum* has a pH optimum of about 5.5 to 6.0, an isoelectric point (pI) of about 7.4 and a molecular weight of about 25 to 28 Kdaltons. EG III cellulase derived from *Trichoderma viride* has a pH optimum of about 5.5, an isoelectric point (pI) of about 7.7 and a molecular weight of about 23.5 Kdaltons.

"Substantially pure EG III cellulase" refers to a composition of cellulase proteins containing at least 40 weight percent, preferably at least 70 weight percent and most preferably at least 90 weight percent of EG III based on the total weight of cellulase proteins.

EG III cellulase can be purified from any strain of Trichoderma spp. which produces EG III under suitable fermentation conditions. While the particular source of EG III is not critical, preferred sources are *Trichoderma longibrachiatum* and *Trichoderma viride*. A particularly preferred source of EG III from *Trichoderma longibrachiatum* is Cytolase 123 cellulase which is commercially available from Genencor International, Inc., 180 Kimball Way, South San Francisco, Calif. 94080. Because of its high pI, EG III is found in a region of an isoelectric focusing gel where high pI xylanases and other high pI components expressed by Trichoderma spp. are generally found. In fact, it has been hypothesized that the band identified as EG III in FIG. 2 was a degradation product of either EG I or II. However, gel isoelectric focusing of EG I and EG II deleted cellulase (prepared in the manner of U.S. Ser. Nos. 07/593,919 and 07/668,640) demonstrated that this band was not attributable to a degradation product of either EG I or II. (See FIG. 2).

It is noted that EG II has been previously referred to by the nomenclature "EG III" by some authors but current nomenclature uses the term "EG II". In any event, the EG II protein is substantially different from the EG III protein in its molecular weight, pI, and pH optimum as evidenced by Table I of Example 2 presented below.

Procedures suitable for obtaining substantially pure EG III cellulase from a complete cellulase system derived from Trichoderma spp. ("whole cellulose") include those recited in the examples set forth herein below. These examples demonstrate that substantially pure EG III cellulase is readily obtained by subjecting whole cellulase to purification procedures including repeated fractionation steps utilizing different fractionation materials (columns). Additionally, the fractionation steps can be preceded by an extraction step using polyethylene glycol 8000 so as to provide for EG III cellulase fraction (about 20–50% pure EG III) which, if necessary, can be used in subsequent fractionation steps to provide for substantially pure EG III cellulase.

Additionally, it is contemplated that substantially pure EG III cellulase can be prepared by genetically modifying microorganisms so as to produce substantially pure EG III cellulase. For example, substantially pure EG III prepared by fractionation methods set forth in the examples below can be employed to determine the amino acid sequence of parts or all of the protein using known sequencing methods. Once the amino acid sequence of parts of the EG III cellulase is known, this information can be used to prepare synthetic DNA probes in order to clone the gene responsible for encoding this information. Once the EG III encoding gene is cloned, it could be manipulated by recognized techniques and ultimately inserted into various Trichoderma spp. strains or into other microorganisms. See, for example, U.S. Ser. No. 07/593,919, filed Oct. 5, 1990 and U.S. Ser. No. 07/668,640, filed Mar. 13, 1991, both of which disclose methods for genetically engineering *Trichoderma longibrachiatum* so that the modified microorganism is incapable of expressing one or more of the cellulase genes and, in fact, may overproduce another cellulase gene. Using the methods described in these applications, *Trichoderma longibrachia-*

*tum* could be genetically manipulated so as to produce EG III with or without other cellulase proteins. Moreover, the methods of these applications create *Trichoderma longibrachiatum* strains which do not produce any heterologous proteins. The disclosures of both U.S. Ser. No. 07/593,919, filed Oct. 5, 1990 and U.S. Ser. No. 07/668,640, filed Mar. 13, 1991, are incorporated herein by reference in their entirety.

Additionally, it would be possible to express the EG III-encoding gene in other microorganisms, including, but not limited to, yeast species such as *Saccharomyces cerevisiae, Pichia pastoris, Hansenula polymorpha, Kluyveromyces lactis, Yarrowia lipolytica, Schanniomyces occidentalis*, etc. See, for example, PCT application Publication No. WO 85/04672. In order to obtain expression in these alternative, non-Trichoderma hosts, it may be necessary to functionally combine the EG III-coding DNA sequence with promoter and terminator sequences obtained from a gene from that particular host. It may also be necessary to substitute the DNA sequence encoding a secretion signal sequence from the alternative host for the DNA sequence encoding the EG III secretion signal sequence. Production and secretion of EG III in other organisms could enable EG III to be obtained in substantially pure form.

"Cellulase proteins" refer to any and all exo-cellobiohydrolase (CBH) proteins, endoglucanase (EG) proteins and β-glucosidase (BG) proteins expressed by a wild type Trichoderma spp. or a transformed strain of Trichoderma spp. Accordingly, cellulase proteins do not include other proteins expressed by Trichoderma spp. including xylanases, proteases, amylases, etc.

"Exo-cellobiohydrolase ("CBH") components" refer to the CBH I and/or CBH II components of *Trichoderma longibrachiatum* and "CBH type components" refer to those fungal cellulase components which exhibit detergent activity properties similar to that of the CBH I and/or CBH II components of *Trichoderma longibrachiatum*. In this regard, when used in the absence of the EG components of *Trichoderma longibrachiatum*, the CBH I and CBH II components of *Trichoderma longibrachiatum* alone do not impart significant color retention/restoration and improved feel to the so-treated cotton-containing fabrics. Additionally, when used in combination with such EG components, the CBH I component of *Trichoderma longibrachiatum* can impart enhanced strength loss and incremental cleaning benefits to cotton-containing fabrics.

Accordingly, CBH I type components and CBH II type components refer to those fungal cellulase components which exhibit detergent activity properties similar to CBH I and CBH II components of *Trichoderma longibrachiatum*, respectively. As noted above, for CBH I type components, this includes the properties of enhancing strength loss of cotton-containing fabrics and/or imparting an incremental cleaning benefit when used in the presence of the EG components of *Trichoderma longibrachiatum*. In a preferred embodiment, the CBH I components also impart an incremental softening benefit when used in the presence of such EG components.

Such CBH type components may exclude components traditionally classified as exo-cellobiohydrolases using activity tests such as those used to characterize CBH I and CBH II from *Trichoderma longibrachiatum*. For example, using such traditional classification tests, such components (a) are competitively inhibited by cellobiose ($K_i$ approximately 1 mM); (b) hydrolyze phosphoric acid swollen cellulose and to a lesser degree highly crystalline cellulose; and (c) are unable to hydrolyze to any significant degree substituted celluloses, such as carboxymethylcellulose, etc. In contrast, it is believed that some CBH components which are characterized as exo-cellobiohydrolase components by such activity tests, do not possess functional properties similar to the CBH components of *Trichoderma longibrachiatum*. Accordingly, it is believed to be more accurate for the purposes herein not to define such exo-cellobiohydrolases as CBH type components because these components do not possess similar functional properties in detergent compositions as possessed by the CBH components of *Trichoderma longibrachiatum*.

"β-Glucosidase (BG) components" refer to those components of cellulase which exhibit BG activity; that is, to say that such components will act from the non-reducing end of cellobiose and other soluble cellooligosaccharides ("cellobiose") and give glucose as the sole product. BG components do not adsorb onto or react with cellulose polymers. Furthermore, such BG components are competitively inhibited by glucose ($K_i$ approximately 1 mM). While in a strict sense, BG components are not literally cellulases because they cannot degrade cellulose, such BG components are included within the definition of the cellulase system because these enzymes facilitate the overall degradation of cellulose by further degrading the inhibitory cellulose degradation products (particularly cellobiose) produced by the combined action of CBH components and EG components. Without the presence of BG components, moderate or little hydrolysis of crystalline cellulose will occur. BG components are often characterized on aryl substrates such as p-nitrophenol B-D-glucoside (PNPG) and thus are often called aryl-glucosidases. It should be noted that not-all aryl-glucosidases are BG components, in that some do not hydrolyze cellobiose.

In some cases, it may be desirable to incorporate BG components into the detergent compositions of this invention (e.g., so as to increase the overall hydrolysis of cellulose if the level of cellobiose becomes restrictive of such overall hydrolysis in the absence of BG components). In such cases, purified BG components can be added to the detergent composition. The amount of BG component added depends upon the amount of cellobiose produced in the detergent wash which can be readily determined by the skilled artisan. However, when employed, the weight percent of BG component relative to total weight of substantially pure EG III cellulase is preferably from about 0.4 to about 10 weight percent, and more preferably, from about 1 to about 5 weight percent.

Fungal cellulases can contain more than one BG component and are generally separated via ion exchange chromatography and the like. In order to facilitate separation, it may be desirable to employ a cellulase composition having increased amounts of BG. Methods to increase the amount of BG components in the cellulase composition are disclosed in U.S. Ser. No. 07/625,140, filed Dec. 10, 1990, and entitled "SACCHARIFICATION OF CELLULOSE BY CLONING AND AMPLIFICATION OF THE β-GLUCOSIDASE GENE OF TRICHODERM REESEI", which application is incorporated herein by reference.

The term "cotton-containing fabric" refers to sewn or unsewn fabrics made of pure cotton or cotton blends including cotton woven fabrics, cotton knits, cotton denims, and the like. When cotton blends are employed, the amount of cotton in the fabric should be at least about 40 percent by weight cotton; preferably, more than about 60 percent by weight cotton; and most preferably, more than about 75 percent by weight cotton. When employed as blends, the companion material employed in the fabric can include one or more non-cotton fibers including synthetic fibers such as polyamide fibers (for example, nylon 6 and nylon 66), acrylic fibers (for example, polyacrylonitrile fibers), polyester fibers (for example, polyethylene terephthalate), polyvinyl alcohol fibers (for example, Vinylon), polyvinyl chloride fibers, polyvinylidene chloride fibers, polyurethane fibers, polyurea fibers and aramid fibers. It is contemplated that regenerated cellulose, such as rayon, could be used as a substitute for cotton in cotton-containing fabrics.

The term "surface active agent or surfactant" refers to anionic, non-ionic and ampholytic surfactants well known for their use in detergent compositions.

The term "wash medium" refers to an aqueous wash solution prepared by adding a requisite amount of a detergent (surfactant) composition to water. The wash medium generally contains a cleaning effective amount of the detergent.

The wash medium is defined as an "acidic wash mediums" if the pH of the medium is from about 4 to less than about 7. The wash medium is defined as a "neutral wash medium" if the pH of the medium is about 7. The wash medium is defined as an "alkaline wash medium" if the pH of the medium is from above 7 to about 10. Preferably, the alkaline wash medium will have a pH of from above 7 to about 9 and, even more preferably, from above 7 to about 8.

The present invention is directed to the discovery that substantially pure EG III cellulase can be used in detergent compositions to effect softening as well as effecting color retention/restoration and improved feel of cotton-containing fabrics regardless of whether such compositions are employed in an acidic, neutral or alkaline wash medium. However, because EG III possesses unexpectedly high activity under alkaline conditions, detergent compositions employing substantially pure EG III cellulase provide enhanced softening, color retention/restoration and improved feel as compared to detergent compositions employing other endoglucanase components derived from *Trichoderma longibrachiatum*.

Although the presence of EG III cellulase effects color retention/restoration, softening and improved feel, specified mixtures of EG III cellulase with other cellulase components can provide some incremental benefits. Specifically, while the use of EG III cellulase will provide a cleaning and softening benefit, incremental cleaning and softening benefits are observed for cotton-containing fabrics washed with a detergent composition containing EG III cellulase and CBH I type cellulose.

On the other hand, the presence of significant amounts of CBH I type components in combination with EG III cellulase may result in enhanced strength loss to cotton-containing fabrics compared to EG III compositions which are either free of CBH I type components or contain reduced amounts of CBH I type components. Accordingly, when the detergent composition contains some CBH I type components, the amount of CBH I type components is preferably no greater than about 10 weight percent, more preferably no greater than about 5 weight percent, and even more preferably less than about 2 weight percent, based on the total weight of cellulose proteins.

In regard to the above, the total amount of substantially pure EG III cellulase generally employed in the detergent compositions of this invention is an amount sufficient to impart color retention/restoration and softness to the cotton garments. Preferably, the substantially pure EG III cellulase composition is employed from about 0.01 weight percent to about 5 weight percent relative to the weight of the total detergent composition. More preferably, substantially pure EG III is employed from about 0.05 weight percent to about 2 weight percent relative to the weight of the total detergent composition. In general, the amount of other cellulase proteins employed in the detergent composition is no more than about 60 weight percent relative to the total weight of cellulase proteins (including EG III cellulase), preferably no more than about 30 weight percent relative to the total weight of cellulose proteins, and more preferably no more than about 10 weight percent relative to the total weight of cellulase proteins. Even more preferably, the CBH type I components preferably do not exceed about 5 weight percent of the total weight of cellulase proteins (i.e., substantially pure EG III cellulose).

The specific concentration of substantially pure EG III cellulase employed in the detergent composition is selected so that upon dilution into a wash medium, the concentration of EG III cellulase will preferably range from about 0.5 to about 500 ppm, and more preferably from about 2 to about 100 ppm. The specific amount of substantially pure EG III cellulase employed in the detergent composition will depend on the extent the detergent composition will be diluted upon addition to water to form a wash medium. These factors are readily ascertained by the skilled artisan.

At lower cellulase concentrations (i.e., concentrations of EG III cellulase of less than about 5 ppm in the wash medium), softness, color retention/restoration and improved feel achieved by use of the detergent compositions of this invention is more evident over repeated washings. At higher concentrations (i.e., concentrations of EG III cellulase of about 5 ppm and above in the wash medium), the improvements can become noticeable in a single wash.

One of the important aspects of the present invention is that by tailoring the cellulase composition to contain substantially pure EG III cellulase, it is possible to achieve the desired effects of softening, color retention/restoration while using lower concentrations of cellulase in the detergent composition. In turn, the use of lower concentrations of cellulase in the detergent compositions should lead to improved consumer safety.

The substantially pure EG III cellulase described above can be added to the detergent composition either in a liquid diluent, in granules, in emulsions, in gels, in pastes, or the like. Such forms are well known to the skilled artisan. When a solid detergent composition is employed, the cellulase composition is preferably formulated as granules. Preferably, the granules can be formulated so as to contain a cellulase protecting agent. See, for instance, U.S. Ser. No. 07/642,669 filed Jan. 17, 1991 as Attorney Docket No. 010055-073 and entitled "GRANULES CONTAINING BOTH AN ENZYME AND AN ENZYME PROTECTING AGENT AND DETERGENT COMPOSITIONS CONTAINING SUCH GRANULES" which application is incorporated herein by reference in its entirety. Likewise, the granule can be formulated so as to contain materials to reduce the rate of dissolution of the granule into the wash medium. Such materials and granules are disclosed in U.S. Ser. No. 07/642,596 filed on Jan. 17, 1991 as Attorney Docket No. GCS-171-US1 and entitled "GRANULAR COMPOSITIONS" which application is incorporated herein by reference in its entirety.

The detergent compositions of this invention employ a surface active agent, i.e., surfactant, including anionic, non-ionic and ampholytic surfactants well known for their use in detergent compositions.

Suitable anionic surfactants for use in the detergent composition of this invention include linear or branched alkylbenzenesulfonates; alkyl or alkenyl ether sulfates having linear or branched alkyl groups or alkenyl groups; alkyl or alkenyl sulfates; olefinsulfonates; alkanesulfonates and the like. Suitable counter ions for anionic surfactants include alkali metal ions such as sodium and potassium; alkaline earth metal ions such as calcium and magnesium; ammonium ion; and alkanolamines having 1 to 3 alkanol groups of carbon number 2 or 3.

Ampholytic surfactants include quaternary ammonium salt sulfonates, betaine-type ampholytic surfactants, and the like. Such ampholytic surfactants have both the positive and negative charged groups in the same molecule, Nonionic surfactants generally comprise polyoxyalkylene ethers, as well as higher fatty acid alkanolamides or alkylene oxide adduct thereof, fatty acid glycerine monoesters, and the like.

Suitable surfactants for use in this invention are disclosed in British Patent Application No. 2 094 826 A, the disclosure of which is incorporated herein by reference.

Mixtures of such surfactants can also be used.

The surfactant or a mixture of surfactants is generally employed in the detergent compositions of this invention in an amount from about 1 weight percent to about 95 weight percent of the total detergent composition and preferably from about 5 weight percent to about 45 weight percent of the total detergent composition. Upon dilution in the wash medium, the surfactant concentration is generally about 500 ppm or more; and preferably, from about 1000 ppm to 15,000 ppm.

In addition to the cellulase composition and the surfactant(s), the detergent compositions of this invention can optionally contain one or more of the following components:

Hydrolases except cellulase

Such hydrolases include carboxylate ester hydrolase, thioester hydrolase, phosphate monoester hydrolase, and phosphate diester hydrolase which act on the ester bond; glycoside hydrolase which acts on glycosyl compounds; an enzyme that hydrolyzes N-glycosyl compounds; thioether hydrolase which acts on the ether bond; and $\alpha$-amino-acyl-peptide hydrolase, peptidyl-amino acid hydrolase, acyl-amino acid hydrolase, dipeptide hydrolase, and peptidyl-peptide hydrolase which act on the peptide bond. Preferable among them are carboxylate ester hydrolase, glycoside hydrolase, and peptidyl-peptide hydrolase. Suitable hydrolases include (1) proteases belonging to peptidyl-peptide hydrolase such as pepsin, pepsin B, rennin, trypsin, chymotrypsin A, chymotrypsin B, elastase, enterokinase, cathepsin C, papain, chymopapain, ficin, thrombin, fibrinolysin, renin, subtilisin, aspergillopeptidase A, collagenase, clostridiopeptidase B, kallikrein, gastrisin, cathepsin D., bromelin, keratinase, chymotrypsin C, pepsin C, aspergillopeptidase B, urokinase, carboxypeptidase A and B, and aminopeptidase; (2) glycoside hydrolases (cellulase which is an essential ingredient is excluded from this group) $\alpha$-amylase, $\beta$-amylase, glucoamylase, invertase, lysozyme, pectinase, chitinase, and dextranase. Preferably among them are $\alpha$-amylase and $\beta$-amylase. They function in acid to neutral systems, but one which is obtained from bacteria exhibits high activity in an alkaline system; (3) carboxylate ester hydrolase including carboxyl esterase, lipase, pectin esterase, and chlorophyllase. Especially effective among them is lipase.

Trade names of commercial products and producers are as follows: "Alkalase", "Esperase", "Savinase", "AMG", "BAN", "Fungamill", "Sweetzyme", "Thermamyl" (Novo Industry, Copenhagen, Denmark); "Maksatase", "High-alkaline protease", "Amylase THC", "Lipase" (Gist Brocades, N.V., Delft, Holland); "Protease B-400", "Protease B-4000", "Protease AP", "Protease AP 2100" (Schweizerische Ferment A.G., Basel, Switzerland); "CRD Protease" (Monsanto Company, St. Louis, Mo.); "Piocase" (Piopin Corporation, Monticello, Ill.); "Pronase P", "Pronase AS", "Pronase AF" (Kaken Chemical Co., Ltd., Japan); "Lapidase P-2000" (Lapidas, Secran, France); protease products (Tyler standard sieve, 100% pass 16 mesh and 100% on 150 mesh) (Clington Corn Products, Division of Standard Brands Corp., New York); "Takamine", "Bromelain 1:10", "HT Protease 200", "Enzyme L-W" (obtained from fungi, not from bacteria) (Miles Chemical Company, Elkhart, Ind.); "Rhozyme P-11 Conc.", "Pectinol", "Lipase B", "Rhozyme PF", "Rhozyme J-25" (Rohm & Haas, Genencor, South San Francisco, Calif.); "Ambrozyme 200" (Jack Wolf & Co., Ltd., Subsidiary of Nopco Chemical Company, Newark, N.J.); "ATP 40", "ATP 120", "ATP 160" (Lapidas, Secran, France); "Oripase" (Nagase & Co., Ltd., Japan).

The hydrolase other than cellulase is incorporated into the detergent composition as much as required according to the purpose. It should preferably be incorporated in an amount of 0.001 to 5 weight percent, and more preferably 0.02 to 3 weight percent, in terms of purified one. This enzyme should be used in the form of granules made of crude enzyme alone or in combination with other components in the detergent composition. Granules of crude enzyme are used in such an amount that the purified enzyme is 0.001 to 50 weight percent in the granules. The granules are used in an amount of 0.002 to 20 and preferably 0.1 to 10 weight percent. As with cellulases, these granules can be formulated so as to contain an enzyme protecting agent and a dissolution retardant material.

Cationic surfactants and long-chain fatty acid salts

Such cationic surfactants and long-chain fatty acid salts include saturated or unsaturated fatty acid salts, alkyl or alkenyl ether carboxylic acid salts, $\alpha$-sulfofatty acid salts or esters, amino acid-type surfactants, phosphate ester surfactants, quaternary ammonium salts including those having 3 to 4 alkyl substituents and up to 1 phenyl substituted alkyl substituents. Suitable cationic surfactants and long-chain fatty acid salts are disclosed in British Patent Application No. 2 094 826 A, the disclosure of which is incorporated herein by reference. The composition may contain from about 1 to about 20 weight percent of such cationic surfactants and long-chain fatty acid salts.

Builders

A. Divalent sequestering agents

The composition may contain from about 0 to about 50 weight percent of one or more builder components selected from the group consisting of alkali metal salts and alkanolamine salts of the following compounds: phosphates, phosphonates, phosphonocarboxylates, salts of amino acids, aminopolyacetates high molecular electrolytes, non-dissociating polymers, salts of dicarboxylic acids, and aluminosilicate salts. Suitable divalent sequestering agents are disclosed in British Patent Application No. 2 094 826 A, the disclosure of which is incorporated herein by reference.

B. Alkalis or inorganic electrolytes

The composition may contain from about 1 to about 50 weight percent, preferably from about 5 to about 30 weight percent, based on the composition of one or more alkali metal salts of the following compounds as the alkalis or inorganic electrolytes: silicates, carbonates and sulfates as well as organic alkalis such as triethanolamine, diethanolamine, monoethanolamine and triisopropanolamine.

Antiredeposition agents

The composition may contain from about 0.1 to about 5 weight percent of one or more of the following compounds as antiredeposition agents: polyethylene glycol, polyvinyl alcohol, polyvinylpyrrolidone and carboxymethylcellulose.

Among them, a combination of carboxymethyl-cellulose or/and polyethylene glycol with the cellulose composition of the present invention provides for an especially useful dirt removing composition.

Bleaching agents

The use of the cellulase of the present invention in combination with a bleaching agent such as sodium percarbonate, sodium perborate, sodium sulfate/hydrogen peroxide adduct and sodium chloride/hydrogen peroxide adduct or/and a photo-sensitive bleaching dye such as zinc or aluminum salt of sulfonated phthalocyanine further improves the deterging effects.

Bluing agents and fluorescent dyes

Various bluing agents and fluorescent dyes may be incorporated in the composition, if necessary. Suitable bluing agents and fluorescent dyes are disclosed in British Patent Application No. 2 094 826 A, the disclosure of which is incorporated herein by reference.

Caking inhibitors

The following caking inhibitors may be incorporated in the powdery detergent: p-toluenesulfonic acid salts, xylenesulfonic acid salts, acetic acid salts, sulfosuccinic acid salts, talc, finely pulverized silica, clay, calcium silicate (such as Micro-Cell of Johns Manville Co.), calcium carbonate and magnesium oxide.

Masking agents for factors inhibiting the cellulase activity

The cellulase compositions of this invention are deactivated in some cases in the presence of copper, zinc, chromium, mercury, lead, manganese or silver ions or their compounds. Various metal chelating agents and metal-precipitating agents are effective against these inhibitors. They include, for example, divalent metal ion sequestering agents as listed in the above item with reference to optional additives as well as magnesium silicate and magnesium sulfate.

Cellobiose, glucose and gluconolactone act sometimes as the inhibitors. It is preferred to avoid the co-presence of these saccharides with the cellulase as far as possible. In case the co-presence is unavoidable, it is necessary to avoid the direct contact of the saccharides with the cellulase by, for example, coating them.

Long-chain-fatty acid salts and cationic surfactants act as the inhibitors in some cases. However, the co-presence of these substances with the cellulase is allowable if the direct contact of them is prevented by some means such as tableting or coating.

The above-mentioned masking agents and methods may be employed, if necessary, in the present invention.

Cellulase-activators

The activators vary depending on variety of the cellulases. In the presence of proteins, cobalt and its salts, magnesium and its salts, and calcium and its salts, potassium and its salts, sodium and its salts or monosaccharides such as mannose and xylose, the cellulases are activated and their deterging powers are improved remarkably.

Antioxidants

The antioxidants include, for example, tert-butyl-hydroxytoluene, 4,4'-butylidenebis(6-tert-butyl-3-methylphenol), 2,2'-butylidenebis(6-tert-butyl-4-methylphenol), monostyrenated cresol, distyrenated cresol, monostyrenated phenol, distyrenated phenol and 1,1-bis(4-hydroxy-phenyl)cyclohexane.

Solubilizers

The solubilizers include, for example, lower alcohols such as ethanol, benzenesulfonate salts, lower alkylbenzene-sulfonate salts such as p-toluenesulfonate salts, glycols such as propylene glycol, acetylbenzene-sulfonate salts, acetamides, pyridinedicarboxylic acid amides, benzoate salts and urea.

The detergent composition of the present invention can be used in a broad pH range of from acidic to alkaline pH. In a preferred embodiment, the detergent composition of the present invention can be used in alkaline detergent wash media and more preferably, alkaline detergent wash media having a pH of from above 7 to no more than about 8.

Aside from the above ingredients, perfumes, buffers, preservatives, dyes and the like can be used, if desired, with the detergent compositions of this invention. Such components are conventionally employed in amounts heretofore used in the art.

When a detergent base used in the present invention is in the form of a powder, it may be one which is prepared by any known preparation methods including a spray-drying method and a granulation method. The detergent base obtained particularly by the spray-drying method and/or spray-drying granulation method are preferred. The detergent base obtained by the spray-drying method is not restricted with respect to preparation conditions. The detergent base obtained by the spray-drying method is hollow granules which are obtained by spraying an aqueous slurry of heat-resistant ingredients, such as surface active agents and builders, into a hot space. The granules have a size of from 50 to 2000 micrometers. After the spray-drying, perfumes, enzymes, bleaching agents, inorganic alkaline builders may be added. With a highly dense, granular detergent base obtained such as by the spray-drying-granulation method, various ingredients may also be added after the preparation of the base.

When the detergent base is a liquid, it may be either a homogeneous solution or an inhomogeneous dispersion. For removing the decomposition of carboxymethylcellulose by the cellulase in the detergent, it is desirable that carboxymethylcellulose is granulated or coated before the incorporation in the composition.

The detergent compositions of this invention are used in industrial and household uses at temperatures and liquor ratios conventionally employed in these environments.

In addition to their use in laundry detergents, substantially pure EG III cellulase described herein can additionally be used in a pre-washing step in the appropriate solution at an intermediate pH where sufficient activity exists to provide desired improvements in color retention/restoration, softening and feel. When the substantially pure EG III cellulase is employed in a pre-soak (e.g., pre-wash) composition, either as a liquid, spray, gel or paste composition, the substantially pure EG III cellulase is generally employed from about 0.01 to about 20 weight percent based on the total weight of the pre-soak composition. In such compositions, a surfactant may optionally be employed and when employed, is generally present at a concentration of from about 0.01 to about 20 weight percent based on the total weight of the pre-soak. The remainder of the composition comprises conventional components used in the pre-soak, i.e., diluent, buffers, other enzymes (proteases), and the like at their conventional concentrations. Accordingly, such pre-soak compositions comprise from about 0 to about 20 weight percent of a surfactant and from about 0.01 to about 20 weight percent of substantially pure EG III cellulase.

Also, it is contemplated that the substantially pure. EG III cellulose described herein can be used in home use as a stand alone composition suitable for restoring color to faded fabrics (see, for example, U.S. Pat. No. 4,738,682, which is incorporated herein by reference in its entirety) as well as used in a spot-remover.

Additionally, it is further contemplated that the high activity under neutral to alkaline conditions for EG III cellulose would be beneficial in textile processes for treating cotton-containing fabrics (see U.S. Ser. Nos. 07/677,385 and 07/678,865 which are incorporated herein by reference in their entirety) as well as in silage and/or composting processes.

The following examples are offered to illustrate the present invention and should not be construed in any way as limiting the scope of this invention.

EXAMPLES

Example 1 demonstrates the isolation of the components other than EG III from Cytolase 123 Cellulase (a complete fungal cellulose composition obtained from *Trichoderma longibrachiatum* and available from Genencor International, Inc., South San Francisco, Calif.) via purification procedures.

Example 1

Purification of Cytolase 123 Cellulase into Cellulase Components

CYTOLASE 123 cellulase was fractionated in the following manner. The normal distribution of cellulase components in this cellulase system is as follows:

| | |
|---|---|
| CBH I | 45–55 weight percent |
| CBH II | 13–15 weight percent |
| EG I | 11–13 weight percent |
| EG II | 8–10 weight percent |
| EG III | 1–4 weight percent |
| BG | 0.5–1 weight percent. |

The fractionation was done using columns containing the following resins: Sephadex G-25 gel filtration resin from Sigma Chemical Company (St. Louis, Mo.), QA Trisacryl M anion exchange resin and SP Trisacryl M cation exchange resin from IBF Biotechnics (Savage, Md.). CYTOLASE 123 cellulase, 0.5 g, was desalted using a column of 3 liters of Sephadex G-25 gel filtration resin with 10 mM sodium phosphate buffer at pH 6.8. The desalted solution, was then loaded onto a column of 20 ml of QA Trisacryl M anion exchange resin. The fraction bound on this column contained CBH I and EG I. These components were separated by gradient elution using an aqueous gradient containing from 0 to about 500 mM sodium chloride. The fraction not bound on this column contained CBH II and EG II. These fractions were desalted using a column of Sephadex G-25 gel filtration resin equilibrated with 10 mM sodium citrate, pH 3.3. This solution, 200 ml, was then loaded onto a column of 20 ml of SP Trisacryl M cation exchange resin. CBH II and EG II were eluted separately using an aqueous gradient containing from 0 to about 200 mM sodium chloride.

Example 2

Purification of EG III from Cytolase 123 Cellulase

Example 1 above demonstrated the isolation of several components from Cytolase 123 Cellulase. However, because EG III is present in very small quantities in Cytolase 123 Cellulase, the following procedures were employed to isolate this component.

A. Large Scale Extraction of EG III Cellulase Enzyme

One hundred liters of cell free cellulase filtrate were heated to about 30° C. The heated material was made about 4% wt/vol PEG 8000 (polyethylene glycol, MW of about 8000) and about 10% wt/vol anhydrous sodium sulfate. The mixture formed a two phase liquid mixture. The phases were separated using an SA-1 disk stack centrifuge. The phases were analyzed using silver staining isoelectric focusing gels. Fractionation and enrichment were obtained for EG III and xylanase. The recovered composition contained about 20 to 50 weight percent of EG III.

Regarding the above procedure, use of a polyethylene glycol having a molecular weight substantially less than about 8000 gave inadequate separation; whereas, use of polyethylene glycol having a molecular weight substantially greater than about 8000 resulted in the exclusion of desired enzymes in the recovered composition. With regard to the amount of sodium sulfate, sodium sulfate levels substantially greater than about 10% wt/vol caused precipitation problems; whereas, sodium sulfate levels substantially less than about 10% wt/vol gave poor separation or the solution remained in a single phase.

B. Purification of EG III Via Fractionation

The purification of EG III is conducted by fractionation from a complete fungal cellulase composition (CYTOLASE 123 cellulose, commercially available from Genencor International, South San Francisco, Calif.) which is produced by wild type *Trichoderma longibrachiatum*. Specifically, the fractionation is done using columns containing the following resins: Sephadex G-25 gel filtration resin from, Sigma Chemical Company (St. Louis, Mo.), QA Trisacryl M anion exchange resin and SP Trisacryl M cation exchange resin from IBF Biotechnics (Savage, Md.). CYTOLASE 123 cellulose, 0.5 g, is desalted using a column of 3 liters of Sephadex G-25 gel filtration resin with 10 mM sodium phosphate buffer at pH 6.8. The desalted solution, is then loaded onto a column of 20 ml of QA Trisacryl M anion exchange resin. The fraction bound on this column contained CBH I and EG I. The fraction not bound on this column contains CBH II, EG II and EG III. These fractions are desalted using a column of Sephadex G-25 gel filtration resin equilibrated with 10 mM sodium citrate, pH 4.5. This solution, 200 ml, is then loaded onto a column of 20 ml of SP Trisacryl M cation exchange resin. The EG III was eluted with 100 mL of an aqueous solution of 200 mM sodium chloride.

In order to enhance the efficiency of the isolation of EG III, it may be desirable to employ *Trichoderma longibrachiatum* genetically modified so as to overexpress EG III and/or to be incapable of producing one or more of EG I, EG II, CBH I and/or CBH II components. This will necessarily lead to more efficient isolation of EG III by, for example, fractionation and/or PEG extraction as described above. Production of some of these strains of *Trichoderma longibrachiatum* are disclosed in U.S. Ser. No. 07/668,640, filed Mar. 13, 1991. Examples of production of some of these strains of *Trichoderma longibrachiatum* as set forth in that application are as follows:

Example 3

Selection for pyr4 mutants of *Trichoderma longibrachiatum*

The pyr4 gene encodes orotidine-5'-monophosphate decarboxylase, an enzyme required for the biosynthesis of uridine. The toxic inhibitor 5-fluoroorotic acid (FOA) is incorporated into uridine by wild-type cells and thus poisons the cells. However, cells defective in the pyr4 gene are resistant to this inhibitor but require uridine for growth. It is, therefore, possible to select for pyr4 mutant strains using FOA. In practice, spores of *Trichoderma longibrachiatum* strain RL-P37 (Sheir-Neiss G. and Montenecourt, B. S., 1984, Appl. Microbiol. Biotechnol. 20:46–53) were spread on the surface of a solidified medium containing 2 mg/ml uridine and 1.2 mg/ml FOA. Spontaneous FOA-resistant colonies appeared within three to four days and it was possible to subsequently identify those FOA-resistant mutants which required uridine for growth. In order to identify those mutants which specifically had a defective pyr4 gene, protoplasts were generated and transformed with a plasmid containing a wild-type pyr4 gene (see Examples 5 and 6). Following transformation, protoplasts were plated on medium lacking uridine. Subsequent growth of transformed colonies demonstrated complementation of a defective pyr4 gene by the plasmid-borne pyr4 gene. In this way strain GC69 was identified as a pyr4 mutant of strain RL-P37.

Example 4

Preparation of CBHI Deletion Vector

A cbh1 gene encoding the CBHI protein was cloned from genomic DNA using strain RL-P37 by hybridization with an oligonucleotide probe designed on the basis of the published sequence for this gene using known probe synthesis methods (Shoemaker et al., "Molecular Cloning of Exo-cellobiohydrolase I Derived from *Trichoderma longibrachiatum* Strain L27", Bio/Technology 1, p. 691 (1983)). The cbh1 gene resides on a 6.5 kb PstI fragment and was inserted into PstI cut pUC4K (purchased from Pharmacia Inc., Piscataway, N.J.) replacing the Kan$^r$ gene of this vector. The resulting plasmid, pUC4K::cbh1 was then cut with HindIII and the larger fragment of about 6 kb was isolated and religated to give pUC4K::cbh1ΔH/H. This procedure removes the entire cbh1 coding sequence and approximately 1.2 kb upstream and 1.5 kb downstream of flanking DNA from either side of the original PstI fragment.

The *Trichoderma longibrachiatum* pyr4 gene was cloned as a 6.5 kb fragment of genomic DNA in pUC18 following the methods of Sambrook et al., 1989, Molecular Cloning, A Laboratory Manual, $2^{nd}$ ED., Cold Springs Harbor Press. The plasmid pUC4K::cbh1ΔH/H was cut with HindIII and the ends were desphosphorylated with calf intestinal alkaline phosphatase. This end dephosphorylated DNA was ligated with the 6.5 kb HindIII fragment containing the *Trichoderma longibrachiatum* pyr4 gene to give pΔCBHIpyr4. See FIG. 4.

Example 5

Isolation of Protoplasts

Mycelium was obtained by inoculating 100 ml of YEG (0.5% yeast extract, 2% glucose) in a 500 ml flask with about $5\times10^7$ *Trichoderma longibrachiatum* GC69 spores (the pyr4mutant strain). The flask was then incubated at 37° C. with shaking for about 16 hours. The mycelium was harvested by centrifugation at 2,750×g. The harvested mycelium was further washed in 1.2M sorbitol solution and resuspended in 40 ml of Novozym$^R$ 234 solution (which is the tradename for a multicomponent enzyme system containing 1,3-alpha-glucanase, 1,3-beta-glucanase, laminarinase, xylanase, chitinase and protease from Novo Biolabs, Danbury Conn.) containing 5 mg/ml Novozym$^R$ 234; 5 mg/ml $MgSO_4.7H_2O$; 0.5 mg/ml bovine serum albumin; 1.2M sorbitol. The protoplasts were removed from cellular debris by filtration through Miracloth (Calbiochem. Corp) and collected by centrifugation at 2,000×g. The protoplasts were washed three times in 1.2M sorbitol and once in 1.2M sorbitol, 50 mM $CaCl_2$, centrifuged and resuspended. The protoplasts were finally resuspended at a density of $2\times10^8$ protoplasts per ml of 1.2M sorbitol, 50 mM $CaCl_2$.

Example 6

Transformation of Fungal Protoplasts

200 μl of the protoplast suspension prepared in Example 5 was added to 20 μl of EcoRI digested pΔCBHIpyr4 (prepared in Example 4) in TE buffer (10 mM Tris, pH 7.4; 1 mM EDTA) and 50 μl of a polyethylene glycol (PEG) solution containing 25% PEG 4000, 0.6M KCl and 50 mM $CaCl_2$. This mixture was incubated on ice for 20 minutes. After this incubation period 2.0 ml of the above-identified PEG solution was added thereto, the solution was further mixed and incubated at room temperature for 5 minutes. After this second incubation, 4.0 ml of a solution containing 1.2M sorbitol and 50 mM $CaCl_2$ was added thereto and this solution was further mixed. The protoplast solution was then immediately added to molten aliquots of Vogel's Medium N (3 grams sodium citrate, 5 grams $KH_2PO_4$, 2 grams $NH_4NO_3$, 0.2 grams $MgSO_4.7H_2O$, 0.1 gram $CaCl_2.2H_2O$, 5 μg α-biotin, 5 mg citric acid, 5 mg $ZnSO_4.7H_2O$, 1 mg $Fe(NH_4)_2.6H_2O$, 0.25 mg $CuSO_4.5H_2O$, 50 μg $MnSO_4.4H_2O$ per liter) containing an additional 1% glucose, 1.2M sorbitol and 1% agarose. The protoplast/medium mixture was then poured onto a solid medium containing the same Vogel's medium as stated above. No uridine was present in the medium and therefore only transformed colonies were able to grow as a result of complementation of the pyr4 mutation of strain GC69 by the wild type pyr4 gene present in pΔCBHIpyr4. These colonies were subsequently transferred and stable transformants purified, on a solid Vogel's medium N containing as an additive, 1% glucose.

Example 7

Analysis of the Transformants

DNA was isolated from the transformants obtained in Example 5 after they were grown in the liquid Vogel's medium N containing 1% glucose. These transformant DNA samples were further cut with a PstI restriction enzyme and subjected to agarose gel electrophoresis. The gel was then further blotted onto a Nytran membrane filter and hybridized with a $^{32}P$ labelled pΔCBHIpyr4 probe. The probe was selected to identify the native cbh1 gene as a 6.5 kb PstI fragment, the native pyr4 gene and any DNA sequences derived from the transforming DNA fragment. FIG. 5 outlines deletion of the *Trichoderma longibrachiatum* cbh1 gene by integration of the larger EcoR1 fragment from pΔCBHIpyr4 at the cbh1 locus on one of the *Trichoderma longibrachiatum* chromosomes.

The bands from the hybridization were visualized via autoradiography. The result of the autoradiograph is seen in FIG. 6. Five samples were run as described above, hence samples A, B, C, D, and E. Lane E is the untransformed strain GC69 and was used as a control in the present analysis. Lanes A–D represent transformants obtained from the methods described above. The numbers on the side of the autoradiograph represent the sizes of molecular weight markers. As can be seen from this autoradiograph, Lane D does not contain the 6.5 kb CBHI band, indicating that this gene has been totally deleted in the transformant. This cbh1 deleted strain is called P37PΔCBHI. The other transformants analyzed appear identical to the untransformed control strain. Presumably, this happened because the linear fragment from pΔCBHIpyr4 integrated by a double crossover at the native pyr4 locus to give a gene replacement event.

Example 8

The same procedure was used in this example as in Example 7, except that the probe used was changed to a $^{32}$P labelled pIntCBHI probe. This probe is a pUC-type plasmid containing a 2 kb BglII fragment from the cbh1 locus within the region that was deleted in pUC4::cbh1ΔH/H. Two samples were run in this example including a control sample A, which is the untransformed strain GC69 and the transformant P37PΔCBHI, sample B. As can be seen in FIG. 7, sample A contained the cbh1 gene, as indicated by the band at 6.5 kb; however the transformant, sample B does not contain this 6.5 kb band and therefore does not contain the cbh1 gene.

Example 9

Protein Secretion by Strain P37PΔCBHI

Spores from the produced P37PΔCBHI strain were inoculated into 50 ml of a Trichoderma basal medium containing 1% glucose, 0.14% $(NH_4)_2SO_4$, 0.2% $KH_2PO_4$, 0.03% $MgSO_4$, 0.03% urea, 0.75% bactotryptone, 0.05% Tween 80, 0.000016% $CuSO_4.5H_2O$, 0.001% $FeSO_4.7H_2O$, 0.000128% $ZnSO_4.7H_2O$, 0.0000054% $Na_2MoO_4.2H_2O$, 0.0000007% $MnCl.4H_2O$). The medium was incubated while shaking in a 250 ml flask at 37° C. for about 48 hours. The resulting mycelium was collected by filtering through Miracloth (Calbiochem Corp.) and washed two or three times with 17 mM potassium phosphate. The mycelium was finally suspended in 17 mM potassium phosphate with 1 mM sophorose and further incubated for 24 hours at 30° C. while shaking. The supernatant was then collected from these cultures and the mycelium was discarded. Samples of the culture supernatant were analyzed by isoelectric focusing using a Pharmacia Phastgel system and pH 3–9 precast gels according to the manufacturer's instructions. The gel was stained with silver stain to visualize the protein bands. The band corresponding to the cbh1 protein was absent from the sample derived from the strain P37PΔCBHI, as shown in FIG. 8. This isoelectric focusing gel shows various proteins in different supernatant cultures of Trichoderma longibrachiatum. Lane A is partially purified CBHI; Lane B is the supernatant from an untransformed Trichoderma longibrachiatum culture; Lane C is the supernatant from a strain deleted for the cbh1 gene produced according to the methods of the present invention. The position of various cellulase components are labelled. Since CBHI constitutes about 50% of the total extra-cellular protein, it is the major secreted protein and hence is the darkest band on the gel. This isoelectric focusing gel clearly shows depletion of the CBHI protein in the strain deleted for cbh1.

Example 10

Preparation of pPΔCBHII

The cbh2 gene of T. longibrachiatum, encoding the CBHII protein, has been cloned as a 4.1 kb EcoRI fragment of genomic DNA which is shown diagrammatically in FIG. 9A (Chen et al., 1987, Biotechnology, 5:274–278). Using methods known in the art, a plasmid, pPΔCBHII (FIG. 9B), has been constructed in which a 3.2 kb central region of this clone between a HindIII site (at 74 bp 3' of the CBHII translation initiation site) and a ClaI site (at 265 bp 3' of the last codon of CBHII) has been removed and replaced by the Trichoderma longibrachiatum pyr4 gene.

Digestion of this plasmid with EcoRI will liberate a fragment having 0.7 kb of flanking DNA from the cbh2 locus at one end, 1.7 kb of flanking DNA from the cbh2 locus at the other end and the Trichoderma longibrachiatum pyr4 gene in the middle.

Example 11

Generation of a pyr4 mutant of P37PΔCBHI

Spores of the transformant (P37PΔCBHI) which was deleted for the cbh1 gene were spread onto medium containing FOA. A pyr4$^-$ derivative of this transformant was subsequently obtained using the methods of Example 3. This pyr4$^-$ strain was designated P37PΔCBHIPyr$^-$26.

Example 12

Deletion of cbh2 gene in a strain previously deleted for cbh1

Protoplasts of strain P37PΔCBHIPyr$^-$26 were generated and transformed with EcoRI digested pPΔCBHII according to the methods outlined in Examples 5 and 6.

Purified stable transformants were cultured in shake flasks as in Example 9 and the protein in the culture supernatants was examined by isoelectric focusing. One transformant (designated P37PΔΔCBH67) was identified which did not produce any CBHII protein. Lane D of FIG. 8 shows the supernatant from a strain deleted for both the cbh1 and cbh2 genes produced according to the methods of the present invention.

DNA was extracted from strain P37PΔΔCBH67, digested with EcoRI and Asp718, and subjected to agarose gel electrophoresis. The DNA from this gel was blotted to a membrane filter and hybridized with 32P labelled pPΔCBHII (FIG. 10). Lane A of FIG. 10 shows the hybridization pattern observed for DNA from an untransformed Trichoderma longibrachiatum strain. The 4.1 kb EcoRI fragment containing the wild-type cbh2 gene was observed. Lane B shows the hybridization pattern observed for strain P37PΔΔCBH67. The single 4.1 kb band has been eliminated and replaced by two bands of approximately 0.9 and 3.1 kb. This is the expected pattern if a single copy of the EcoRI fragment from pPΔCBHII had integrated precisely at the cbh2 locus.

The same DNA samples were also digested with EcoRI and Southern analysis was performed as above. In this example, the probe was $^{32}$P labelled pIntCBHII. This plasmid contains a portion of the cbh2 gene coding sequence from within that segment of cbh2 DNA which was deleted in plasmid pPΔCBHII. No hybridization was seen with DNA from strain P37PΔΔCBH67 showing that the cbh2 gene was deleted and that no sequences derived from the pUC plasmid were present in this strain.

Example 13

Construction of pEGIpyr4

The Trichoderma longibrachiatum egl1 gene, which encodes EGI, has been cloned as a 4.2 kb HindIII fragment of genomic DNA from strain RL-P37 by hybridization with oligonucleotides synthesized according to the published sequence (Penttila et al., 1986, Gene 45:253–263). A 3.6 kb HindIII-BamHI fragment was taken from this clone and ligated with a 1.6 kb HindIII-BamHI fragment containing the *Trichoderma longibrachiatum* pyr4 gene and a pUC-based plasmid cut with HindIII to give the plasmid pEGIyr4 (FIG. 11). Digestion of pEGIpyr4 with HindIII would liberate a fragment of DNA containing only *Trichoderma longibrachiatum* genomic DNA (the egl1 and pyr4 genes) except for 24 bp of sequenced, synthetic DNA between the two genes and 6 bp of sequenced, synthetic DNA at one end (see FIG. 11).

Example 14

Transformants of *Trichoderma longibrachiatum* containing pEGIpyr4

A pyr4 defective mutant of *Trichoderma longibrachiatum* strain RutC30 (Sheir-Neiss and Montenecourt, 1984, Appl. Microbiol. Biotechnol. 20:46–53) was obtained by the method outlined in Example 3. Protoplasts of this strain were transformed with undigested pEGIpyr4 and stable transformants were purified. Five of these transformants (designated EP2, EP4, EP5, EP6, EP11), as well as untransformed RutC30 were inoculated into 50 ml of YEG medium (yeast extract, 5 g/l; glucose, 20 g/l) in 250 ml shake flasks and cultured with shaking for 2 days at 28° C. The resulting mycelium was washed with sterile water and added to 50 ml of TSF medium (0.05M citrate-phosphate buffer, pH 5.0; Avicel microcrystalline cellulose, 10 g/l; $KH_2PO_4$, 2.0 g/l; $(NH_4)_2SO_4$, 1.4 g/l; proteose peptone, 1.0 g/l; Urea, 0.3 g/l; $MgSO_4.7H_2O$, 0.3 g/l; $CaCl_2$, 0.3 g/l; $FeSO_4.7H_2O$, 5.0 mg/l; $MnSO_4.H_2O$, 1.6 mg/l; $ZnSO_4$, 1.4 mg/l; $CoCl_2$, 2.0 mg/l; 0.1 % Tween 80). These cultures were incubated with shaking for a further 4 days at 28° C. Samples of the supernatant were taken from these cultures and assays designed to measure the total amount of protein and of endoglucanase activity were performed as described below.

The endoglucanase assay relied on the release of soluble, dyed oligosaccharides from Remazol Brilliant Blue—carboxymethylcellulose (RBB-CMC, obtained from MegaZyme, North Rocks, NSW, Australia). The substrate was prepared by adding 2 g of dry RBB-CMC to 80 ml of just boiled deionized water with vigorous stirring. When cooled to room temperature, 5 ml of 2M sodium acetate buffer (pH 4.8) was added and the pH adjusted to 4.5. The volume was finally adjusted to 100 ml with deionized water and sodium azide added to a final concentration of 0.02%. Aliquots of *Trichoderma longibrachiatum* culture supernatant or 0.1M sodium acetate as a blank (10–20 μl) were placed in tubes, 250 μl of substrate was added and the tubes were incubated for 30 minutes at 37° C. The tubes were placed on ice for 10 minutes and 1 ml of cold precipitant (3.3% sodium acetate, 0.4% zinc acetate, pH 5 with HCl, 76% ethanol) was then added. The tubes were vortexed and allowed to sit for 5 minutes before centrifuging for 3 minutes at approximately 13,000×g. The optical density was measured spectrophotometrically at a wavelength of 590–600 nm.

The protein assay used was the BCA (bicinchoninic acid) assay using reagents obtained from Pierce, Rockford, Ill., USA. The standard was bovine serum albumin (BSA). BCA reagent was made by mixing 1 part of reagent B with 50 parts of reagent A. One ml of the BCA reagent was mixed with 50 μl of appropriately diluted BSA or *Trichoderma longibrachiatum* culture supernatant. Incubation was for 30 minutes at 37° C. and the optical density was finally measured spectrophotometrically at a wavelength of 562 nm.

It is clear that some of the transformants produced increased amounts of endoglucanase activity compared to untransformed strain RutC30. It is thought that the endoglucanases or exo-cellobiohydrolases produced by untransformed *Trichoderma longibrachiatum* constitute approximately 20% and 70% respectively of the total amount of protein secreted. Therefore a transformant such as EP5, which produces approximately four-fold more endoglucanase than strain RutC30, would be expected to secrete approximately equal amounts of endoglucanase-type and exo-cellobiohydrolase-type proteins.

The transformants described in this example were obtained using intact pEGIpyr4 and will contain DNA sequences integrated in the genome which were derived from the pUC plasmid. Prior to transformation it would be possible to digest pEGIpyr4 with HindIII and isolate the larger DNA fragment containing only *Trichoderma longibrachiatum* DNA. Transformation of *Trichoderma longibrachiatum* with this isolated fragment of DNA would allow isolation of transformants which overproduced EGI and contained no heterologous DNA sequences except for the two short pieces of synthetic DNA shown in FIG. 11. It would also be possible to use pEGIpyr4 to transform a strain which was deleted for either the cbh1 gene, or the cbh2 gene, or for both genes. In this way a strain could be constructed which would over-produce EGI and produce either a limited range of, or no, exo-cellobiohydrolases.

The methods of Example 14 could be used to produce *Trichoderma longibrachiatum* strains which would over-produce any of the other endoglucanases normally produced by *Trichoderma longibrachiatum* (*T. longibrachiatum*).

Likewise, it may be desirable for the EG III is compositions described above to be further purified. For example, EG III protein isolated in procedures A or B above can be further purified by utilizing material obtained from procedure A in procedure B or vice versa. One particular method for further purifying EG III is by further fractionation of an EG III sample obtained in part b) of this Example 2. The further fraction was done on a FPLC system using a Mono-S-HR 5/5 column (available from Pharmacia LKB Biotechnology, Piscataway, N.J.). The FPLC system consists of a liquid chromatography controller, 2 pumps, a dual path monitor, a fraction collector and a chart recorder (all of which are available from Pharmacia LKB Biotechnology, Piscataway, N.J.). The fractionation was conducted by desalting 5 ml of the EG III sample prepared in part b) of this Example 2 with a 20 ml Sephadex G-25 column which had been previously equilibrated with 10 mM sodium citrate pH 4. The column was then eluted with 0–200 mM aqueous gradient of NaCl at a rate of 0.5 ml/minute with samples collected in 1 ml fractions. EG III was recovered in fractions 10 and 11 and was determined to be greater than 90% pure by gel electrophoresis. EG III of this purity is suitable for determining the N-terminal amino acid sequence by known techniques.

Substantially pure EG III has the following characteristics which are compared to the other endoglucanases isolated from *Trichoderma longibrachiatum*.

TABLE I

| | MW | pI | pH optimum[1] |
|---|---|---|---|
| EG I | ~47–49 kD | 4.7 | ~5 |
| EG II | ~35 kD | 5.5 | ~5 |
| EG III | ~25–28 kD | 7.4 | ~5.5–6.0 |

[1] pH optimum determined by RBB-CMC activity as per Example 3 below.

As can be seen from the above table, EG III has both a higher pH optimum and a higher pI as compared to the other endoglucanase components of *Trichoderma longibrachiatum*. In Example 3 below, it is seen that EG III also retains significant RBB-CMC activity under alkaline pHs.

Likewise, EG III cellulase from other strains of Trichoderma spp. can be purified. For example, EG III cellulase derived from *Trichoderma viride* has been described by Voragen et al., Methods in Enzymology, 16:243–249. This reference describes the EG III cellulase as having a molecular weight of about 23.5 Kdaltons, a pH optimum of 5.5, and a pI of 7.7.

Example 15

Activity of Cellulase Compositions over a pH Range

The following procedure was employed to determine the pH profiles of two different cellulase compositions. The first cellulase composition was a CBH I and II deleted cellulase composition prepared from *Trichoderma longibrachiatum* genetically modified in a manner similar to that described above so as to be unable to produce CBH I and CBH II components. Insofar as this cellulase composition does not contain CBH I and CBH II which generally comprise from about 58 to 70 percent of a cellulose composition derived from *Trichoderma longibrachiatum*, this cellulose composition is necessarily enriched in EG components. Since EG III is the most minor of the endoglucanase components of *Trichoderma longibrachiatum*, this composition predominates in EG I and EG II components.

The second cellulase composition was an approximately 20–40% pure fraction of EG III isolated from a cellulase composition derived from *Trichoderma longibrachiatum* via purification methods similar to part b) of Example 2.

The activity of these cellulase compositions was determined at 40° C. and the determinations were made using the following procedures.

Add 5 to 20 μl of an appropriate enzyme solution at a concentration sufficient to provide the requisite amount of enzyme in the final solution. Add 250 μl of 2 weight percent RBB-CMC (Remazol Brilliant Blue R-Carboxymethylcellulose—commercially available from MegaZyme, 6 Altona Place, North Rocks, N.S.W. 2151, Australia) in 0.05M citrate/phosphate buffer at pH 4, 5, 5.5, 6, 6.5, 7, 7.5 and 8.

Vortex and incubate at 40° C. for 30 minutes. Chill in an ice bath for 5 to 10 minutes. Add 1000 μl of methyl cellosolve containing 0.3M sodium acetate and 0.02M zinc acetate. Vortex and let sit for 5–10 minutes. Centrifuge and pour supernatant into cuvets.

Relative enzyme activity was determined by measuring the optical density (OD) of the solution in each cuvet at 590 nm. Higher levels of optical density correspond to higher levels of enzyme activity.

The results of this analysis are set forth in FIG. 1 which illustrates the relative activity of the CBH I and II deleted cellulase composition compared to the EG III cellulase composition. From this figure, it is seen that the cellulase composition deleted in CBH I and CBH II possesses optimum cellulolytic activity against RBB-CMC at near pH 5.5 and has some activity at alkaline pHs, i.e., at pHs from above 7 to 8. on the other hand, the cellulose composition enriched in EG III possesses optimum cellulolytic activity at about pH 5.5–6 and possesses significant activity at alkaline pHs.

Example 16

Isoelectric Focusing Gels

The purpose of this example is to illustrate isoelectric focusing gels of different EG III cellulase compositions. Specifically, cellulase produced by a wild type *Trichoderma longibrachiatum*; cellulase derived from a strain of *Trichoderma longibrachiatum* transformed so as to be incapable of expressing EG I and EG II cellulase proteins; and substantially pure EG III cellulase were analyzed on isoelectric focusing gels.

Samples of these cellulases were analyzed by isoelectric focusing using a Pharmacia IEF system (FBE-3000, Pharmacia Inc., Piscataway, N.J.) and pH 3–10 precast gels (Servalyt Precote, available from Serva, Carl-Berg, Germany) according to the manufacturer's instructions. The gels were stained with Ephortec™ stain (Serva Blue W, available from Serva Fine Biochemicals, Westbury, N.Y. 11590) stain to visualize the protein bands. The resulting gel is set forth in FIG. 2 wherein Lane 1 of FIG. 2 illustrates the isoelectric focusing gel of cellulase derived from a wild strain *Trichoderma longibrachiatum*; Lane 2 illustrates the isoelectric focusing gel of cellulase derived from a strain of *Trichoderma longibrachiatum* so as to be incapable of expressing EG I and II; and Lane 3 illustrates the isoelectric focusing gel of substantially pure EG III cellulase. In this figure, the margin adjacent to Lane 1 is marked to identify the bands corresponding to cellulose proteins so as to permit identification of the proteins.

From the above figure, it is seen that because of EG III's high pI, this protein is found in a region usually associated with other high pI components such as high pI xylanases, high pI β-glucosidases, etc. Moreover, this figure demonstrates that EG III is not a degradation product of either EG I or EG II proteins because, in Lane 2 of this figure, these proteins are not present while the EG III protein is.

Example 17

Color Restoration

The ability of EG III cellulase to restore color in cotton-containing fabrics was analyzed in the following experiment. Specifically, reduced color clarity in a worn cotton fabric arises from the accumulation on the fabric of surface fibers over a period of time. These fibers give rise to a faded and matted appearance for the fabric and accordingly, the removal of these fibers is a necessary prerequisite to restoring the original sharp color to the fabric. In view of the above, this experiment determines the ability of EG III cellulase to restore color by measuring the ability of the EG III cellulose to remove surface fibers.

In this experiment, two different compositions were compared for the ability to remove fiber. Specifically, the first composition contains substantially pure EG III cellulase (prepared in a manner similar to that set forth in Example 2) whereas the second composition contains no EG III cellulase or any other cellulase composition.

In this example, an appropriate amount of cellulase (if employed) was added to separate solutions of 400 ml of a 20 mM citrate/phosphate buffer containing 0.5 ml of a nonionic surfactant. Samples were prepared and titrated so as to provide for samples at pH 6, pH 7, pH 8 and pH 9. Each of the resulting solutions was then added to a separate launderometer canister. Into these canisters were added a quantity of marbles to facilitate fiber removal as well as a 7 inch×5 inch cotton fabric (100% woven cotton, available as Style No. 439W from Test Fabrics, Inc., 200 Blackford Ave., Middlesex, N.J. 08846). The canister was then closed and the canister lowered into the launderometer bath which was maintained at 43° C. The canister was then rotated in the bath at a speed of at least about 40 revolutions per minute (rpms) for about 1 hour. Afterwards, the cloth is removed, rinsed well and dried in a standard drier.

The so treated fabrics were then analyzed for fiber removal by evaluation in a panel test. In particular, the fabrics (unmarked) were rated for levels of fiber by 6 individuals. The fabrics were visually evaluated for surface fibers and rated on a 1 to 7 scale. The scale has seven standards to allow for meaningful comparisons. The standards are:

| Rating | Standard[a] |
|---|---|
| 7 | Fabric not treated with cellulase |
| 6 | Fabric treated[b] with 8 ppm cellulase |
| 5 | Fabric treated with 16 ppm cellulase |
| 4 | Fabric treated with 20 ppm cellulase |
| 3 | Fabric treated with 40 ppm cellulase |
| 2 | Fabric treated with 50 ppm cellulase |
| 1 | Fabric treated with 100 ppm cellulase |

[a]In all of the standards, the fabric was a 100% cotton sheeting standardized test fabric (Style No. 439W) available from Test Fabrics, Inc., 200 Blackford Ave., Middlesex, NJ 08846
[b]For all samples treated with the same cellulase composition. Cellulase concentrations are in total protein. The launderometer treatment conditions are the same as set forth in Example 16 above.

The fabric to be rated was provided a rating which most closely matched one of the standards. After complete analysis of the fabrics, the values assigned to each fabric by all of the individuals were added and an average value generated. In these results, lower numbers correspond to improved fiber removal.

The results of this analysis are set forth in FIG. 3 which illustrates that at acidic, neutral and alkaline pH's, substantially pure EG III cellulase provides for fiber removal.

What is claimed is:

1. A detergent composition suitable for use with cotton-containing fabrics which comprises:

a cleaning effective amount of a surfactant or a mixture of surfactants suitable for preparing an alkaline wash medium having a pH of from above 7 to about 10 and from about 0.01 to about 5 weight percent of a cellulase composition comprising at least 40 weight percent of endoglucanase III based on the total weight of exo-cellobiohydrolase, endoglucanase and β-glucosidase proteins in the cellulase composition wherein said endoglucanase III is an endoglucanase component derived from any strain of Trichoderma spp. which produces endoglucanase III and having a pH optimum of about 5.5 to 6.0, an isoelectric point of from about 7.2 to 8.0, and a molecular weight of about 23 to 28 Kdaltons.

2. A detergent composition according to claim 1 wherein said cellulase composition comprises from about 0.05 to about 2 weight percent of said detergent composition.

3. A detergent composition according to claim 1 wherein said detergent composition is free of exo-cellobio-hydrolase I component.

4. A detergent composition according to claim 3 wherein said cellulase composition is further free of exo-cellobiohydrolase II component.

5. A detergent composition according to claim 1 wherein said cellulase composition is derived from *Trichoderma longibrachiatum*.

6. A detergent composition according to claim 1 wherein said cellulase composition is derived from *Trichoderma viride*.

7. A detergent composition according to claim 1 wherein said surfactant or mixture of surfactants is suitable for preparing an alkaline wash medium having a pH of from about 7 to about 8.

* * * * *